United States Patent
Wei

(10) Patent No.: US 8,768,460 B2
(45) Date of Patent: *Jul. 1, 2014

(54) PAIN FREE DEFIBRILLATION THRESHOLD ESTIMATION

(75) Inventor: Xuan Wei, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 213 days.

This patent is subject to a terminal disclaimer.

(21) Appl. No.: 13/010,540

(22) Filed: Jan. 20, 2011

(65) Prior Publication Data

US 2011/0112594 A1    May 12, 2011

Related U.S. Application Data

(63) Continuation of application No. 11/695,711, filed on Apr. 3, 2007, now Pat. No. 7,890,167.

(51) Int. Cl.
*A61N 1/39* (2006.01)

(52) U.S. Cl.
USPC .................. 607/8; 607/5; 607/7; 607/28

(58) Field of Classification Search
USPC ................................ 607/5, 7, 8, 28
See application file for complete search history.

(56) References Cited

U.S. PATENT DOCUMENTS

| | | | |
|---|---|---|---|
| 4,727,877 A | 3/1988 | Kallok | |
| 5,269,300 A | 12/1993 | Kelly et al. | |
| 5,318,597 A | 6/1994 | Hauck et al. | |
| 5,346,506 A | 9/1994 | Mower et al. | |
| 5,350,401 A | 9/1994 | Levine | |
| 5,350,406 A | 9/1994 | Nitzsche et al. | |
| 5,354,316 A | 10/1994 | Keimel | |
| 5,397,336 A | 3/1995 | Hirschberg et al. | |
| 5,531,770 A | 7/1996 | Kroll et al. | |
| 5,540,724 A | 7/1996 | Cox | |
| 5,554,174 A | 9/1996 | Causey, III | |
| 5,662,687 A | 9/1997 | Hedberg et al. | |
| 5,683,431 A | 11/1997 | Wang | |
| 5,713,924 A | 2/1998 | Min et al. | |

(Continued)

FOREIGN PATENT DOCUMENTS

| | | |
|---|---|---|
| EP | 1928548 B1 | 2/2012 |
| JP | 5015933 B2 | 9/2012 |

(Continued)

OTHER PUBLICATIONS

"Application Serial No. 06789564.9, Office Action mailed Aug. 6, 2009", 7 pgs.

(Continued)

*Primary Examiner* — Carl H Layno
*Assistant Examiner* — Jennifer Ghand
(74) *Attorney, Agent, or Firm* — Schwegman Lundberg & Woessner, P.A.

(57) ABSTRACT

A system and method for painlessly calculating an estimated defibrillation threshold, such as by using an implantable medical device and a controller. The estimated defibrillation threshold can be calculated using a delivered first energy to a first thoracic location, an electric field detected at a second thoracic location, and an electric field detected between a third thoracic location and a fourth thoracic location. The estimated defibrillation threshold represents an energy that, when delivered at the first thoracic location, can create an electric field strength in a target region of the heart that meets or exceeds a target electric field strength.

20 Claims, 8 Drawing Sheets

(56) References Cited

U.S. PATENT DOCUMENTS

| | | | |
|---|---|---|---|
| 5,722,994 | A | 3/1998 | Noren et al. |
| 5,738,105 | A | 4/1998 | Kroll |
| 5,749,901 | A | 5/1998 | Bush et al. |
| 5,836,975 | A | 11/1998 | DeGroot |
| 5,836,976 | A | 11/1998 | Min et al. |
| 5,851,220 | A | 12/1998 | Murphy |
| 5,925,067 | A | 7/1999 | Lu |
| 5,954,752 | A | 9/1999 | Mongeon et al. |
| 5,974,340 | A | 10/1999 | Kadhiresan |
| 5,978,705 | A | 11/1999 | KenKnight et al. |
| 5,999,852 | A | 12/1999 | Elabbady et al. |
| 6,076,015 | A | 6/2000 | Hartley et al. |
| 6,169,923 | B1 | 1/2001 | Kroll |
| 6,278,894 | B1 | 8/2001 | Salo et al. |
| 6,353,761 | B1 | 3/2002 | Conley et al. |
| 6,363,281 | B1 | 3/2002 | Zhu et al. |
| 6,415,179 | B1 | 7/2002 | Pendekanti et al. |
| 6,445,949 | B1 | 9/2002 | Kroll |
| 6,487,443 | B2 | 11/2002 | Olson et al. |
| 6,628,986 | B1 | 9/2003 | Mouchawar et al. |
| 6,675,042 | B2 | 1/2004 | Swerdlow et al. |
| 6,751,502 | B2 | 6/2004 | Daum et al. |
| 6,859,664 | B2 | 2/2005 | Daum et al. |
| 6,904,314 | B1 | 6/2005 | Brewer et al. |
| 6,949,075 | B2 | 9/2005 | Hatlestad et al. |
| 6,978,178 | B2 | 12/2005 | Sommer et al. |
| 7,643,877 | B2 | 1/2010 | Dujmovic, Jr. et al. |
| 7,711,425 | B2 | 5/2010 | Wei et al. |
| 7,890,167 | B2 | 2/2011 | Wei |
| 8,036,744 | B2 | 10/2011 | Dujmovic et al. |
| 2002/0002389 | A1 | 1/2002 | Bradley et al. |
| 2002/0123768 | A1 | 9/2002 | Gilkerson et al. |
| 2002/0133206 | A1 | 9/2002 | Daum et al. |
| 2002/0169483 | A1 | 11/2002 | Henry et al. |
| 2002/0188215 | A1 | 12/2002 | Ferek-Petric |
| 2002/0188326 | A1 | 12/2002 | Zheng et al. |
| 2003/0032989 | A1 | 2/2003 | Herleikson |
| 2003/0088282 | A1 | 5/2003 | Ostroff |
| 2003/0105491 | A1 | 6/2003 | Gilkerson et al. |
| 2003/0120312 | A1 | 6/2003 | Cammilli et al. |
| 2003/0120316 | A1 | 6/2003 | Spinelli et al. |
| 2003/0195569 | A1 | 10/2003 | Swerdlow et al. |
| 2004/0138714 | A1 | 7/2004 | Daum et al. |
| 2005/0251215 | A1 | 11/2005 | Dujmovic et al. |
| 2007/0043395 | A1 | 2/2007 | Wei et al. |
| 2008/0249581 | A1 | 10/2008 | Wei |
| 2010/0087884 | A1 | 4/2010 | Dujmovic, Jr. et al. |

FOREIGN PATENT DOCUMENTS

| | | |
|---|---|---|
| JP | 5027294 82 | 9/2012 |
| WO | WO-2007024471 A1 | 3/2007 |
| WO | WO-2008123902 A1 | 10/2008 |

OTHER PUBLICATIONS

"U.S. Appl. No. 09/808,419, Amendment and Response filed Oct. 15, 2003 to Non-Final Office Action mailed Jul. 16, 2003", 14 pgs.
"U.S. Appl. No. 09/808,419, Amendment and Response filed Dec. 6, 2002 to Non-Final Office Action mailed Sep. 10, 2002", 14 pgs.
"U.S. Appl. No. 09/808,419, Non-Final Office Action mailed Jul. 16, 2003", 7 pgs.
"U.S. Appl. No. 09/808,419, Non-Final Office Action mailed Sep. 10, 2002", 7 pgs.
"U.S. Appl. No. 09/808,419, Notice of Allowance mailed Jan. 17, 2003", 8 pgs.
"U.S. Appl. No. 09/808,419, Notice of Allowance mailed Nov. 24, 2003", 7 pgs.
"U.S. Appl. No. 09/808,419, Notice of Allowance mailed Feb. 26, 2004", 6 pgs.
"U.S. Appl. No. 10/744,991, Notice of Allowance mailed Sep. 21, 2004", 7 pgs.
"U.S. Appl. No. 11/061,315, Response filed Apr. 7, 2008 to Restriction Requirement mailed Mar. 6, 2008", 8 pgs.
"U.S. Appl. No. 11/061,315, Restriction Requirement mailed Mar. 6, 2008", 8 pgs.
"U.S. Appl. No. 11/061,315, Final Office Action mailed Apr. 3, 2009", 12 pgs.
"U.S. Appl. No. 11/061,315, Pre-Appeal Brief Request for Review filed Jul. 6, 2009", 5 pgs.
"U.S. Appl. No. 11/061,315, Response filed Jan. 22, 2009 Non Final Office Action mailed Jul. 25, 2008", 12 pgs.
"U.S. Appl. No. 11/061315, Non-Final Office Action mailed Jul. 25, 2008", 10 pgs.
"U.S. Appl. No. 11/208,923, Restriction Requirement mailed Jun. 6, 2008", 5 pgs.
"U.S. Appl. No. 11/208,923, Response filed Jan. 21, 2009 to Non Final Office Action mailed Sep. 17, 2008", 16 pgs.
"U.S. Appl. No. 11/208,923, Response filed Jul. 7, 2008 to Restriction Requirement mailed Jun. 6, 2008", 12 pgs.
"U.S. Appl. No. 11/208,923, Final Office Action mailed Apr. 3, 2009", 10 pgs.
"U.S. Appl. No. 11/208,923, Non-Final Office Action mailed Sep. 17, 2008", 9 pgs.
"U.S. Appl. No. 11/208,923, Notice of Allowance mailed Dec. 17, 2009", 8 pgs.
"U.S. Appl. No. 11/208,923, Notice of Panel Decision mailed Jul. 30, 2009", 2 pgs.
"U.S. Appl. No. 11/208,923, Pre-Appeal Brief Request for Review filed Jul. 6, 2009", 4 pgs.
"U.S. Appl. No. 11/695,711 Notice of Allowance mailed Oct. 6, 2010", 11 pgs.
"U.S. Appl. No. 11/695,711, Non-Final Office Action mailed Jan. 29, 2010", 10 pgs.
"U.S. Appl. No. 11/695,711, Response filed Nov. 6, 2000 to Restriction mailed Oct. 7, 2009", 13 pgs.
"U.S. Appl. No. 11/695,711, Response filed May 26, 2010 to Non Final Office Action mailed Jan. 29, 2010", 24 pgs.
"U.S. Appl. No. 11/695,711, Restriction Requirement Received Oct. 7, 2009", 5.
"European Application No. 08725287.0, Office Action Mailed Feb. 25, 2010", 4 pgs.
"European Application No. 08725287.0, Response filed Aug. 24, 2010 to Office Action mailed Feb. 25, 2010", 9 pgs.
"European Application U.S. Appl. No. 06789564.9, Communication mailed Aug. 6, 2009", 7 pgs.
"European Application U.S. Appl. No. 06789564.9, Communication mailed Jul. 15, 2008", 4 pgs.
"European Application U.S. Appl. No. 06789564.9, Response filed Jan. 26, 2009 to Communication mailed Jul. 15, 2008", 24 pgs.
"European Application U.S. Appl. No. 06789564.9, Response filed Feb. 15, 2010 to Communication mailed Aug. 6, 2009", 8 pgs.
"International Application U.S. Appl. No. PCT/US2006/030829, International Search Report and Written Opinion mailed Dec. 13, 2006", 13 pgs.
"International Application U.S. Appl. No. PCT/US2008/001637, International Search Report mailed Jul. 9, 2008", 5 pgs.
"International Application U.S. Appl. No. PCT/US2008/001637, Written Opinion mailed Jul. 9, 2008", 8 pgs.
Bessho, R., et al., "Measurement of the upper limit of vulnerability during defibrillator implantation can substitute defibrillation threshold measurement", The International Journal of Artificial Organs, 21 (3), (Mar. 1998), 151-160.
Birgersdotter-Green, Ulrika, et al., "Correlation of Acute and Chronic Defibrillation Threshold with Upper Limit of Vulnerability Determined in Normal Sinus Rhythm", Journal of Interventional Cardiac Electrophysiology, 3, (Mar. 1999), 155-161.
Church, T., et al., "A Model to Evaluate Alternative Methods of Defibrillation Threshold Determination", PACE, 11, (Nov. 1988), pp. 2002-2007.
Eason, J., et al., "Influence of Anisotropy on Local and Global Measures of Potential Gradient in Computer Models of Defibrillation", Annals of Biomedical Engineering, 26, (1998), pp. 840-849.
Ellenbogen, K. A., et al., "Immediate Reproducibility of Upper Limit of Vulnerability Measurements in Patients Undergoing Transvenous Implantable Cardioverter Defibrillator Implantation", Journal of Cardiovascular Electrophysiology, 9 (6), (Jun. 1998), pp. 588-595.

(56) References Cited

OTHER PUBLICATIONS

Ideker, R. E., "Chapter 2—Mechanisms of Defibrillation", Defibrillation of the heart : ICDs, AEDs, and manual, St. Louis : Mosby, (1994), 15-45.

Martin, D. J., et al., "Upper Limit of Vulnerability Predicts Chronic Defibrillation Threshold for Transvenous Implantable Defibrillators", Journal of Cardiovascular Electrophysiology, 8 (3), (Mar. 1997), 241-248.

Min, X., et al., "Finite element analysis of defibrillation fields in a human torso model for ventricular defibrillation", Progress in Biophysics & Molecular Biology, 69, (1998), pp. 353-386.

Pendekanti, R., et al., "Spatial Potential and Current Distributions Along Transvenous Defibrillation Electrodes: Variation of Electrode Characteristics", Annals of Biomedical Engineering, 24, (1996), pp. 156-167.

Schimpf, P. H., et al., "Effects of electrode interface impedance of finite element models of transvenous defibrillation", Medical & Biological Engineering & Computing, (Sep. 1995), pp. 713-719.

Sun, Weimin, et al., "DFT Test Via Pacing Measurements without VF Induction and Shocking", PACE, vol. 23, Abstract No. 235, (Apr. 2000), 1 pg.

Swerdlow, C. D., et al., "Comparative Reproducibility of Defibrillation Threshold and Upper Limit of Vulnerability", PACE, 19, (Dec. 1996), pp. 2103-2111.

Swerdlow, C. D., et al., "Programming of Implantable Cardioverter-Defibrillators on the Basis of the Upper Limit of Vulnerability", Circulation, 95 (6), (Mar. 18, 1997), pp. 1497-1504.

Swerdlow, Charles, et al., "Determination of the Upper Limit of Vulnerability Using Implantable Cardioverter-Defibrillator Electrograms", Circulation, 107, (Jun. 24, 2003), 3028-3033.

Wang, Y., et al., "Analysis of Defibrillation Efficacy from Myocardial Voltage Gradients with Finite Element Modeling", IEEE Transactions on Biomedical Engineering, 46 (9), (1999), pp. 1025-1036.

"U.S. Appl. No. 11/061,315, Notice of Allowance mailed Aug. 17, 2009", 6 pgs.

"U.S. Appl. No. 11/208,923, Notice of Allowance mailed Aug. 28, 2009", 8 pgs.

"U.S. Appl. No. 12/631,944, Non-Final Office Action mailed Nov. 29, 2010", 10 pgs.

"U.S. Appl. No. 12/631,944, Notice of Allowance mailed Jun. 14, 2011", 8 pgs.

"U.S. Appl. No. 12/631,944, Response filed Mar. 28, 2011 to Non-Final Office Action mailed Nov. 29, 2010", 9 pgs.

"U.S. Appl. No. 12/631,944, Response filed Oct. 27, 2010 to Restriction Requirement mailed Oct. 1, 2010", 8 pgs.

"U.S. Appl. No. 12/631,944, Restriction Requirement mailed Oct. 1, 2010", 6 pgs.

"Japanese Application U.S. Appl. No. 2008-527952, Office Action mailed Jan. 10, 2012", (w/ English Translation), 8 pgs.

"Japanese Application Serial No. 2008-527952, Response filed Apr. 5, 2012 to Office Action.mailed Jan. 1, 2012", (w/ English Translation of Claims), 14 pgs.

"Japanese Application Serial No. 2010-502070, Office Action mailed Feb. 7, 2012", (w/ English Translation), 4 pgs.

"Japanese Application Serial No. 2010-502070, Response filed May 7, 2012 to Office Action mailed Feb. 9, 2012", (w/ English Translation of Amended Claims), 11 pgs.

Fromer, M., et al., "Experience with a New Implantable Pacer-, Cardioverter-Defibrillator for the Therapy of Recurrent Sustained Ventricular Tachyarrhythmias: A Step Toward a Universal Ventricular Tachyarrhythmia Control Device", Journal of Pacing and Clinical Electrophysiology, 14, (1991), 1288-1297.

Pinski, S. L., et al., "Permanent Pacing via Implantable Defibrillators", Journal of Pacing and Clinical Electrophysioiogy, 23(11 Part 1), (2000), 1667-1682.

Saksena, S., et al., "Long-Term Multicenter Experience With a Second-Generation Implantable Pacemaker-Defibrillator in Patients With Malignant Ventricular Tachyarrhythmias", Journal of American College of Cardiology, 19(3), (1992), 490-499.

```
                                    ┌─1100
                                   /
                        ┌─1105
┌─────────────────────────────────────────┐
│  PROVIDE A NOTIFICATION USING INFORMATION ABOUT AT LEAST ONE │
│  ESTIMATED DEFIBRILLATION THRESHOLD OR A DETECTED ELECTRIC FIELD │
└─────────────────────────────────────────┘
```

*FIG. 11*

```
                                    ┌─1200
                                   /
                        ┌─1205
┌─────────────────────────────────────────┐
│  SENSE AT LEAST ONE OF A HEART SIGNAL AND A RESPIRATION SIGNAL │
└─────────────────────────────────────────┘
                         │
                         ▼
                        ┌─1210
┌─────────────────────────────────────────┐
│  DELIVER A FIRST ENERGY AT A SPECIFIED PORTION OF AT LEAST ONE │
│       OF THE HEART SIGNAL AND THE RESPIRATION SIGNAL        │
└─────────────────────────────────────────┘
```

*FIG. 12*

```
                                    ┌─1300
                                   /
                        ┌─1305
┌─────────────────────────────────────────┐
│  SENSE AT LEAST ONE OF A HEART SIGNAL AND A RESPIRATION SIGNAL │
└─────────────────────────────────────────┘
                         │
                         ▼
                        ┌─1310
┌─────────────────────────────────────────┐
│  DETECT A FIRST ELECTRIC FIELD OR A SECOND ELECTRIC FIELD AT A │
│  SPECIFIED PORTION OF AT LEAST ONE OF THE HEART SIGNAL AND THE │
│                    RESPIRATION SIGNAL                        │
└─────────────────────────────────────────┘
```

*FIG.13*

PAIN FREE DEFIBRILLATION THRESHOLD ESTIMATION

CLAIM OF PRIORITY

This application is a continuation of and claims the benefit of priority under 35 U.S.C. §120 to Wei, U.S. patent application Ser. No. 11/695,711, entitled "PAIN FREE DEFIBRILLATION THRESHOLD ESTIMATION," filed on Apr. 3, 2007, which is hereby incorporated by reference herein in its entirety.

CROSS-REFERENCE TO RELATED APPLICATIONS

This application is related to the commonly assigned Wei et al. U.S. patent application Ser. No. 11/208,923 entitled "DEFIBRILLATION THRESHOLD PREDICTION METHODS AND SYSTEMS," (herein "Wei et al. '923") filed on Aug. 22, 2005; and the commonly assigned Daum et al. U.S. Pat. No. 6,751,502 entitled "CARDIAC RHYTHM MANAGEMENT SYSTEM WITH DEFIBRILLATION THRESHOLD PREDICTION," (herein "Daum et al. '502") filed on Sep. 19, 2002; the disclosures of which are hereby incorporated by reference.

TECHNICAL FIELD

This patent document pertains generally to implantable medical devices, and more particularly, but not by way of limitation, to defibrillation threshold estimation.

BACKGROUND

When functioning properly, a heart maintains its own rhythm and is capable of pumping a sufficient amount of blood throughout a subject's circulatory system. However, some subjects may have cardiac arrhythmia. Generally, cardiac arrhythmia is a condition or group of conditions characterized by an irregular cardiac rhythm. In certain examples, cardiac arrhythmia can result in a diminished blood circulation throughout the body.

A cardiac arrhythmia can be treated using a cardiac rhythm management system. A cardiac rhythm management system can include an implantable or external system or device, such as a defibrillator, configured to deliver therapy, such as an electric stimulus, to the heart. Generally, a defibrillator can be used to deliver an electric stimulus, typically referred to as a defibrillation countershock or shock. The defibrillation countershock can interrupt an abnormal heart rhythm, allowing the heart to reestablish normal rhythm.

One problem faced by a cardiac rhythm management system is the determination of a threshold energy required, for a particular defibrillation shock waveform, to reliably convert an abnormal heart rhythm to normal heart rhythm. Ventricular fibrillation and atrial fibrillation are probabilistic phenomena that generally observe a dose-response relationship with respect to shock strength. The ventricular defibrillation threshold is the smallest amount of energy that can be delivered to the heart to reliably revert ventricular fibrillation or fast ventricular tachycardia to normal rhythm. Similarly, the atrial defibrillation threshold is the threshold amount of energy that will reliably terminate an atrial fibrillation. The defibrillation thresholds can vary from subject to subject, and may even vary within a subject depending on the placement of a lead or an electrode used to deliver the energy or depending on the subject's condition.

One technique for determining a defibrillation threshold includes inducing a targeted tachyarrhythmia (e.g., ventricular fibrillation), and then applying one or more than one shock of varying magnitude to determine the energy needed to convert the arrhythmia to normal heart rhythm. However, this technique requires imposing the risks and discomfort associated with both the arrhythmia and the defibrillation. Electric energy delivered to the heart has the potential to both cause myocardial injury or pain. As a result, anesthesia is generally required, adding an additional logistic barrier for implementation. Moreover, if defibrillation thresholds are being obtained in order to assist a physician in determining an optimal lead placement, these disadvantages are compounded as the procedure is repeated for different potential lead placements.

Another technique for determining the defibrillation threshold, referred to as the "upper limit of vulnerability" technique, includes shocking a subject that is in a state of normal heart rhythm during a vulnerable period of the cardiac cycle. The vulnerable period is generally a period when the heart tissue is undergoing repolarization, e.g., a R-wave period. Typically, one or more than one shock of varying magnitude is applied until fibrillation is induced. After such fibrillation is induced, the subject must again be shocked in order to interrupt the arrhythmia and reestablish normal heart rhythm. In this technique, the corresponding fibrillation-inducing shock magnitude is related, through a theoretical model, to a defibrillation threshold energy. The upper limit of vulnerability technique also suffers from imposing the risks and discomfort associated with both the arrhythmia and the defibrillation shock.

Moreover, because of the discomfort associated with the fibrillation and shocks, the subject is typically sedated under general anesthesia, which itself imposes additional risk and increased cost. For these and other reasons, the present inventor has recognized a need to estimate a defibrillation threshold without relying on a defibrillation countershock to induce or terminate an actual arrhythmia.

Overview

This document discusses, among other things, a system and method for painlessly calculating an estimated defibrillation threshold using an implantable medical device and a controller. The implantable medical device can include a first energy delivery circuit, a second energy delivery circuit, a first electric field detector, and a second electric field detector. The estimated defibrillation threshold can be calculated using a delivered first energy to a first thoracic location, an electric field detected at a second thoracic location, and an electric field detected between a third thoracic location and a fourth thoracic location. The estimated defibrillation threshold represents an energy that, when delivered at the first thoracic location, can create an electric field strength in a target region of the heart that meets or exceeds a target electric field strength.

In Example 1, a system includes an implantable medical device and an implantable or external controller. The implantable medical device includes a first energy delivery circuit, configured to deliver a nondefibrillating and nonfibrillation-inducing energy to a first thoracic location, wherein the first thoracic location includes at least one thoracic location, a first electric field detector, configured to detect an electric field, from the delivered nondefibrillating and nonfibrillation-inducing energy to the first thoracic location, at a second thoracic location, wherein the second thoracic location includes at least one thoracic location, and a second electric field detector, configured to detect an electric field between a third thoracic location, which is at or near the first thoracic location, and a fourth thoracic location, which is at or near the second thoracic location. The implantable or external controller is communicatively coupled to the first energy delivery circuit, the first electric field detector, and the second electric field detector, and is configured to calculate an estimated defibrillation threshold using the nondefibrillating and non-fibrillation-inducing energy delivered to the first thoracic location, the electric field detected at the second thoracic location, and the electric field detected between the third thoracic location and the fourth thoracic location.

In Example 2, the first energy delivery circuit of Example 1 optionally includes at least one of a voltage source and a current source, and is optionally configured to deliver at least one of a voltage and a current using at least one first electrode and at least one second electrode.

In Example 3, the first thoracic location of Examples 1-2 optionally includes in, on, or near a first chamber of a heart.

In Example 4, the first thoracic location of Examples 1-3 optionally includes a location in, on, or near at least one of a right ventricle of the heart, a superior vena cava, an internal pectoral region, and an internal abdominal region.

In Example 5, the second thoracic location of Examples 1-4 optionally includes a location in, on, or near at least one of an apical region of a heart and a lateral wall of the heart.

In Example 6, the second thoracic location of Examples 1-5 optionally includes a location in, on, or near at least one of a left apical region of the heart and a left ventricular free lateral wall of the heart.

In Example 7, the estimated defibrillation threshold ("$VDFT1_{est}$") of Examples 1-6 is optionally calculated using the equation:

$$VDFT1_{est} = V_1 \frac{A}{\nabla V_2} \frac{1}{(aV_{3-4} + b + 1)},$$

wherein $V_1$ includes the nondefibrillating and nonfibrillation-inducing energy delivered to the first thoracic location, wherein A is the minimal potential gradient for a successful defibrillation, wherein $\nabla V_2$ includes the resulting response signal detected at the second thoracic location, wherein $V_{3-4}$ includes the electric field detected between the third thoracic location and the fourth thoracic location, and wherein a and b are coefficients.

In Example 8, the coefficients a and b of Examples 1-7 are optionally calculated using a relationship between at least one known defibrillation threshold and the detected second electric field.

In Example 9, the controller of Examples 1-8 is optionally configured to calculate an estimated defibrillation threshold using the nondefibrillating and nonfibrillation-inducing energy delivered to the first thoracic location and the electric field detected at the second thoracic location, and wherein the controller is configured to adjust the estimated defibrillation threshold using the electric field detected between the third thoracic location and the fourth thoracic location.

In Example 10, the estimated defibrillation threshold ("$VDFT2_{est}$") of Examples 1-9 is optionally calculated using the equation:

$$VDFT2_{est} = V_1 \frac{A}{\nabla V_2},$$

wherein $V_1$ includes the nondefibrillating and nonfibrillation-inducing energy delivered to the first thoracic location, wherein A is the minimal potential gradient for a successful defibrillation, wherein $\nabla V_2$ includes the electric field detected at the second thoracic location, and wherein the adjusted estimated defibrillation threshold ("$VDFT_{adj}$") is calculated using the equation:

$$VDFT_{adj} = VDFT2_{est} \frac{1}{(aV_{3-4} + b + 1)},$$

wherein $V_{3-4}$ includes the signal detected between the third thoracic location and the fourth thoracic location, and wherein a and b are coefficients.

In Example 11, the coefficients a and b of Examples 1-10 are optionally calculated using a relationship between at least one known defibrillation threshold and the detected second electric field.

In Example 12, the first electric field detector of Examples 1-11 optionally includes the second electric field detector.

In Example 13, the detected electric field between the third thoracic location and the fourth thoracic location of Examples 1-12 optionally includes an electric field from the delivered nondefibrillating and nonfibrillation-inducing energy to the first thoracic location.

In Example 14, the implantable medical device of Examples 1-13 optionally includes a second energy delivery circuit, communicatively coupled to the controller, wherein the second energy delivery circuit is configured to deliver a nondefibrillating and nonfibrillation-inducing energy to a fifth thoracic location, wherein the fifth thoracic location includes at least one thoracic location. The electric field detected between the third thoracic location and the fourth thoracic location of Examples 1-13 also optionally includes an electric field, from the delivered nondefibrillating and nonfibrillation-inducing energy to the fifth thoracic location, between the third thoracic location and the fourth thoracic location.

In Example 15, the fifth thoracic location of Examples 1-14 is optionally at or near at least one of the first thoracic location and the third thoracic location.

In Example 16, the system of Examples 1-15 optionally includes at least one lead, configured to couple at least one of the first energy delivery circuit, the first electric field detector, and the second electric field detector to at least one of the first thoracic location, the second thoracic location, the third thoracic location, and the fourth thoracic location, and wherein the at least one lead includes at least one electrode.

In Example 17, the at least one electrode of Examples 1-16 is optionally configured in a first electrode configuration. The controller of Examples 1-16 is optionally configured to select a second electrode configuration, calculate a second estimated defibrillation threshold for the second electrode configuration, compare the second estimated defibrillation threshold to another estimated defibrillation threshold, and select an estimated defibrillation threshold using at least one of the second estimated defibrillation threshold and the other estimated defibrillation threshold.

In Example 18, the system of Examples 1-17 optionally includes at least one first electrode, configured to couple the first energy delivery circuit to the first thoracic location, and at least one second electrode, configured to couple the first electric field detector to the second thoracic location.

In Example 19, the system of Examples 1-18 optionally includes at least one third electrode, configured to couple the second electric field detector to the third thoracic location, and at least one fourth electrode, configured to couple the second electric field detector to the fourth thoracic location.

In Example 20, the first electrode of Examples 1-19 optionally includes the third electrode. The second electrode of Examples 1-19 also optionally includes the fourth electrode.

In Example 21, the controller of Examples 1-20 is optionally configured to compare at least one of the electric field detected at the second thoracic location to at least one previous electric field detected at the second thoracic location to detect a change in the detected electric field, the electric field detected between the third thoracic location and the fourth thoracic location to at least one previous electric field detected between the third thoracic location and the fourth thoracic location to detect a change in the detected electric field, and the estimated defibrillation threshold to a previous estimated defibrillation threshold to detect a change in the estimated defibrillation threshold.

In Example 22, the controller of Examples 1-21 is optionally configured to detect a change in the estimated defibrillation threshold using at least one of the detected change in the detected electric field at the second thoracic location and the detected change in the electric field between the third thoracic location and the fourth thoracic location.

In Example 23, the system of Examples 1-22 optionally includes a notification module, communicatively coupled to the controller, wherein the notification module is configured to provide a notification using information from the controller.

In Example 24, the system of Examples 1-23 optionally includes at least one of an implantable or external heart signal sensing circuit, communicatively coupled to the controller, configured to sense a heart signal of a heart, and an implantable or external respiration sensor, communicatively coupled to the controller, configured to sense a respiration signal. The first energy delivery circuit of Examples 1-23 is also optionally configured to deliver the nondefibrillating and nonfibrillation-inducing energy to the first thoracic location at a specified portion of at least one of the heart signal of the heart and the respiration signal.

In Example 25, the system of Examples 1-24 optionally includes at least one of an implantable or external heart signal sensing circuit, communicatively coupled to the controller, configured to sense a heart signal of a heart, and an implantable or external respiration sensor, communicatively coupled to the controller, configured to sense a respiration signal. The first electric field detector or the second electric field detector of Examples 1-24 is also optionally configured to detect an electric field at a specified portion of at least one of the heart signal of the heart and the respiration signal.

In Example 26, the controller of Examples 1-25 is optionally configured to compare the estimated defibrillation threshold to a threshold.

In Example 27, a system includes means for delivering a first nondefibrillating and nonfibrillation-inducing energy to a first thoracic location, such as by using the first energy delivery circuit, wherein the first thoracic location includes at least one thoracic location, such as in, on, or near at least one of a first chamber of a heart, a right ventricle of the heart, a superior vena cava, an internal pectoral region, and an internal abdominal region. The system also includes means for detecting an electric field, from the delivered first nondefibrillating and nonfibrillation-inducing energy to the first thoracic location, such as by using the first electric field detector, at a second thoracic location, such as in, on, or near at least one of a left apical region of the heart and a left ventricular free lateral wall of the heart, wherein the second thoracic location includes at least one thoracic location. The system also includes means for detecting an electric field between a third thoracic location, which is at or near the first thoracic location, and a fourth thoracic location, which is at or near the second thoracic location, such as by using the second electric field detector, and further, means for calculating an estimated defibrillation threshold using the first nondefibrillating and nonfibrillation-inducing energy delivered to the first thoracic location, the electric field detected at the second thoracic location, and the electric field detected between the third thoracic location and the fourth thoracic location, such as by using the implantable or external controller.

In Example 28, a method includes delivering a first nondefibrillating and nonfibrillation-inducing energy to a first thoracic location, wherein the first thoracic location includes at least one thoracic location, detecting an electric field, from the delivered first nondefibrillating and nonfibrillation-inducing energy to the first thoracic location, at a second thoracic location, wherein the second thoracic location includes at least one thoracic location, detecting an electric field between a third thoracic location, which is at or near the first thoracic location, and a fourth thoracic location, which is at or near the second thoracic location, and calculating an estimated defibrillation threshold using the first nondefibrillating and nonfibrillation-inducing energy delivered to the first thoracic location, the electric field detected at the second thoracic location, and the electric field detected between the third thoracic location and the fourth thoracic location.

In Example 29, the delivering the first nondefibrillating and nonfibrillation-inducing energy to the first thoracic location of Example 28 optionally includes delivering at least one of a voltage and a current using at least one first electrode and at least one second electrode.

In Example 30, the delivering the first nondefibrillating and nonfibrillation-inducing energy to the first thoracic location of Examples 28-29 optionally includes delivering the first nondefibrillating and nonfibrillation-inducing energy in, on, or near a first chamber of a heart.

In Example 31, the delivering the first nondefibrillating and nonfibrillation-inducing energy in, on, or near the first chamber of the heart of Examples 28-30 optionally includes delivering the first nondefibrillating and nonfibrillation-inducing energy in, on, or near at least one of a right ventricle of the heart, a superior vena cava, an internal pectoral region, and an internal abdominal region.

In Example 32, the detecting the electric field at the second thoracic location of Examples 28-31 optionally includes detecting the electric field in, on, or near at least one of an apical region of a heart and a lateral wall of the heart.

In Example 33, the detecting the electric field in, on, or near at least one of an apical region of the heart and the lateral wall of the heart of Examples 28-32 optionally includes detecting the electric field in, on, or near at least one of a left apical region of the heart and a left ventricular free lateral wall of the heart.

In Example 34, the calculating the estimated defibrillation threshold ("$VDFT1_{est}$") of Examples 28-33 optionally includes using the equation:

$$VDFT1_{est} = V_1 \frac{A}{\nabla V_2} \frac{1}{(aV_{3-4} + b + 1)},$$

wherein $V_1$ includes the first nondefibrillating and nonfibrillation-inducing energy delivered to the first thoracic location, wherein A is the minimal potential gradient for a successful defibrillation, wherein $\nabla V_2$ includes the resulting response signal detected at the second thoracic location, wherein $V_{3-4}$ includes the electric field detected between the third thoracic location and the fourth thoracic location, and wherein a and b are coefficients.

In Example 35, the determining coefficients a and b of Examples 28-34 optionally includes using a relationship between at least one known defibrillation threshold and the detected second electric field.

In Example 36, the calculating an estimated defibrillation threshold of Examples 28-35 optionally includes using the first nondefibrillating and nonfibrillation-inducing energy delivered to the first thoracic location and the electric field detected at the second thoracic location. The method of Examples 28-35 also optionally includes calculating an adjusted estimated defibrillation threshold using the electric field detected between the third thoracic location and the fourth thoracic location.

In Example 37, the calculating the estimated defibrillation threshold ("VDFT2$_{est}$") of Examples 28-36 optionally includes using the equation:

$$VDFT2_{est} = V_1 \frac{A}{\nabla V_2},$$

wherein $V_1$ includes the first nondefibrillating and nonfibrillation-inducing energy delivered to the first thoracic location, wherein A is the minimal potential gradient for a successful defibrillation, wherein $\nabla V_2$ includes the electric field detected at the second thoracic location; and wherein calculating the adjusted estimated defibrillation threshold ("VDFT$_{adj}$") includes using the equation:

$$VDFT_{adj} = VDFT2_{est} \frac{1}{(aV_{3-4} + b + 1)},$$

wherein $V_{3-4}$ includes the signal detected between the third thoracic location and the fourth thoracic location, and wherein a and b are coefficients.

In Example 38, the determining coefficients a and b of Examples 28-37 optionally includes using a relationship between at least one known defibrillation threshold and the detected second electric field.

In Example 39, the detecting the electric field at the second thoracic location and detecting the electric field between the third thoracic location and the fourth thoracic location of Examples 28-38 optionally includes using at least one electric field detector.

In Example 40, the detecting the electric field between the third thoracic location and the fourth thoracic location of Examples 28-39 optionally includes detecting the electric field from the delivered first nondefibrillating and nonfibrillation-inducing energy.

In Example 41, the method of Examples 28-40 optionally includes delivering a second nondefibrillating and nonfibrillation-inducing energy to a fifth thoracic location, wherein the fifth thoracic location includes at least one thoracic location. The detecting the electric field between the third thoracic location and the fourth thoracic location of Examples 28-40 also optionally includes detecting the electric field from the delivered second nondefibrillating and nonfibrillation-inducing energy.

In Example 42, the delivering the second nondefibrillating and nonfibrillation-inducing energy to the fifth thoracic location of Examples 28-41 optionally includes delivering the second nondefibrillating and nonfibrillation-inducing energy at or near at least one of the first location and the third location.

In Example 43, at least one of delivering the first nondefibrillating and nonfibrillation-inducing energy to the first thoracic location, detecting the electric field at the second thoracic location, and detecting the electric field between the third thoracic location and the fourth thoracic location of Examples 28-42 optionally includes using at least one lead.

In Example 44, the delivering the first nondefibrillating and nonfibrillation-inducing energy to the first thoracic location of Examples 28-43 optionally includes using at least one first electrode; and wherein detecting the electric field at the second thoracic location includes using at least one second electrode.

In Example 45, the detecting the electric field between the third thoracic location and the fourth thoracic location of Examples 28-44 optionally includes using at least one third electrode and at least one fourth electrode.

In Example 46, the using the at least one first electrode of Examples 28-45 optionally includes using the at least one third electrode; and wherein using the at least one second electrode includes using the at least one fourth electrode.

In Example 47, the delivering the first nondefibrillating and nonfibrillation-inducing energy to the first thoracic location, detecting the electric field at the second thoracic location, and detecting the electric field between the third thoracic location and the fourth thoracic location of Examples 28-46 optionally includes using at least one electrode configured in a first electrode configuration. The method of Examples 28-46 also optionally includes selecting a second electrode configuration, calculating a second estimated defibrillation threshold for the second electrode configuration, comparing the second estimated defibrillation threshold to another estimated defibrillation threshold, and selecting an estimated defibrillation threshold using at least one of the second estimated defibrillation threshold and the other estimated defibrillation threshold.

In Example 48, the method of Examples 28-47 optionally includes comparing at least one of the electric field detected at the second thoracic location to at least one previous electric field detected at the second thoracic location to detect a change in the detected electric field at the second thoracic location, the electric field detected between the third thoracic location and the fourth thoracic location to at least one previous electric field detected between the third thoracic location and the fourth thoracic location to detect a change in the detected electric field between the third thoracic location and the fourth thoracic location, and the estimated defibrillation threshold to a previous estimated defibrillation threshold to detect a change in the estimated defibrillation threshold.

In Example 49, the method of Examples 28-48 optionally includes detecting a change in the estimated defibrillation threshold using at least one of the detected change in the detected electric field at the second thoracic location and the detected change in the electric field between the third thoracic location and the fourth thoracic location.

In Example 50, the method of Examples 28-49 optionally includes providing a notification using information about at least one detected electric field.

In Example 51, the method of Examples 28-50 optionally includes at least one of sensing a heart signal of a heart and sensing a respiration signal, and wherein delivering the first nondefibrillating and nonfibrillation-inducing energy to the first thoracic location includes delivering at a specified portion of at least one of the heart signal of the heart and the respiration signal.

In Example 52, the method of Examples 28-51 optionally includes at least one of sensing a heart signal of a heart and sensing a respiration signal, and wherein detecting the electric field at the second thoracic location or detecting the electric field between the third thoracic location and the fourth thoracic location includes detecting at a specified portion of at least one of the heart signal of the heart and the respiration signal.

In Example 53, the method of Examples 28-52 optionally includes comparing the estimated defibrillation threshold to a threshold.

In Example 54, the delivering the first nondefibrillating and nonfibrillation-inducing energy to the first thoracic location, detecting the electric field at the second thoracic location, and detecting the electric field between the third thoracic location and the fourth thoracic location of Examples 28-53 optionally includes using at least one lead in a first lead configuration. The method of Examples 28-53 also optionally includes using at least one lead in a second lead configuration, if the estimated defibrillation threshold meets or exceeds the threshold, to calculate a second estimated defibrillation threshold, and comparing the second estimated defibrillation threshold to the threshold.

In Example 55, the method of Examples 28-54 optionally includes providing a notification using information about at least one detected electric field.

This overview is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals can describe substantially similar components throughout the several views. Like numerals having different letter suffixes can represent different instances of substantially similar components. The drawings illustrate generally, by way of example, but not by way of limitation, various embodiments discussed in the present document.

FIG. 11 illustrates generally an example of a portion of a method including providing a notification using information about at least one estimated defibrillation threshold or a detected electric field.

FIG. 12 illustrates generally an example of portions of a method including sensing at least one of a heart signal and a respiration signal. The method further includes delivering a first energy at a specified portion of at least one of the heart signal and the respiration signal.

FIG. 13 illustrates generally an example of portions of a method including sensing at least one of a heart signal and a respiration signal. The method further includes detecting a first electric field or a second electric field at a specified portion of at least one of the heart signal and the respiration signal.

DETAILED DESCRIPTION

Figure 1:
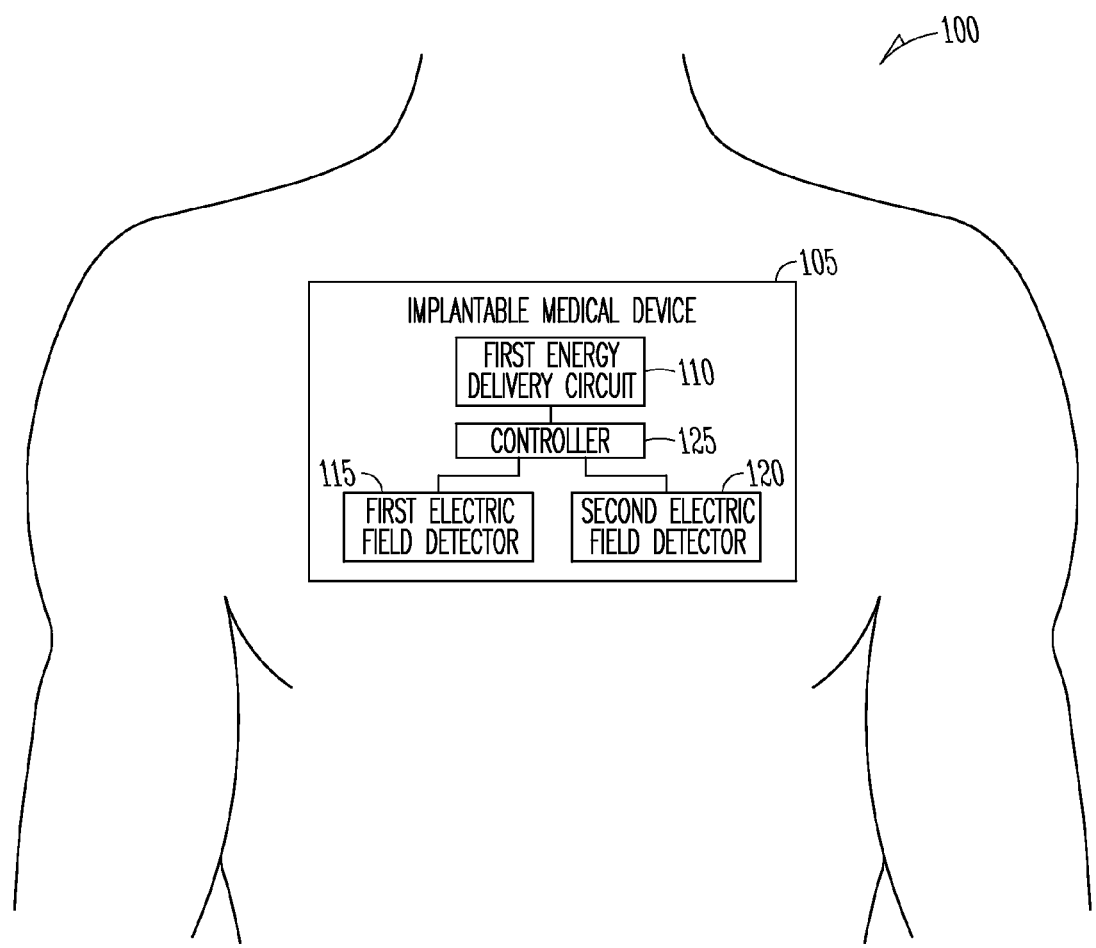
FIG. 1 illustrates generally an example of a system including an implantable medical device, which includes a first energy delivery circuit, a first electric field detector, a second electric field detector, and a controller.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated. Throughout this document, a "user" refers to a physician or other caregiver who examines, treats, or contacts a subject of the type referred to in this document. Also throughout this document, internal locations or regions include subcutaneous locations or regions. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Generally, an estimated defibrillation threshold energy can be determined using an applied electric field strength in a target region of the heart. In order to ensure the efficacy of the defibrillation, to increase or maximize the longevity of the source of energy, or to reduce myocardial energy, the estimated defibrillation threshold can be determined so that the defibrillation energy can be safely set above a specified value, such as to include a safety margin, but low enough so as to not waste energy, shorten the usable life of the implanted device, or exceed the capabilities of an implanted device.

In an example, an energy can be delivered at a first thoracic location, such as a location in, on, or near a first chamber of the heart. In an example, the first thoracic location can include a right ventricle ("RV") of the heart, a superior vena cava, an internal pectoral region, or an internal abdominal region. The energy delivered at the first thoracic location can include a nondefibrillating or nonfibrillation-inducing energy. An electric field can be detected at a second thoracic location in or near the target region of the heart. In an example, the target region of the heart can include in, on, or near the left apical region of the heart, such as the left apical region of the left ventricle ("LV") of the heart, or a left free lateral wall, such as the left free lateral wall of the left ventricle of the heart. The electric field detected at the second thoracic location can be used to estimate the defibrillation threshold energy that will create the desired electric field strength in the target region. In an example, the estimated defibrillation threshold, such as an estimated ventricular defibrillation threshold or an estimated atrial defibrillation threshold, energy can be determined using the desired, or "target", electric field strength, e.g., 5 volts/cm, the energy delivered at the first thoracic location, and the electric field detected at the second thoracic location.

However, in this example, the electric field detected at the second thoracic location can vary with lead location. Generally, electric field intensity decreases as the distance from the energy source increases. If the lead location or the electrode location at the second thoracic location is close to the energy delivery source, then the electric field detected at the second thoracic location will generally be larger than the electric field in or near the target region of the heart, such as in, on, or near the left apical region of the heart or the left free lateral wall of the heart. In this example, using the electric field detected at the second thoracic location could underestimate the estimated defibrillation threshold.

Thus, in an example, an electric field can be detected between a third thoracic location and a fourth thoracic location. The third thoracic location can include a thoracic location at or near the first thoracic location, such as the right ventricle of the heart, and the fourth thoracic location can include a thoracic location at or near the second thoracic location, such as at least one of left apical region of the heart and a left ventricular free lateral wall of the heart. The electric field detected between the third thoracic location and the fourth thoracic location can be indicative of the distance between the third thoracic location and the fourth thoracic location. Or, the electric field detected between the third thoracic location and the fourth thoracic location can be used to accommodate distance variation between the third thoracic location and the fourth thoracic location. In an example, an estimated atrial or ventricular defibrillation threshold energy can be determined using the desired, or "target", electric field strength, e.g., 5 volts/cm, the electric field detected at the first thoracic location, the electric field detected at the second thoracic location, and the electric field detected between the third thoracic location and the fourth thoracic location. In an example, using the electric field detected at the second thoracic location or the electric field detected between the third thoracic location and the fourth thoracic location can avoid reliance on fluoroscopic distance measurement or electric field modeling computations, can account for variation in lead or electrode location, or can account for vasculature difference between subjects.

An change in a defibrillation threshold or an electric field (such as the electric field detected between the third thoracic location and the fourth thoracic location) can be indicative of hypertrophy, ventricle dilation, ischemia, myocardial infarction, scar tissue, lead dislodgement, or subject condition change. In an example, when a change in the electric field is detected, when estimated defibrillation threshold is detected, or when the estimated defibrillation threshold value meets or exceeds a particular threshold value, a defibrillation energy can be increased or decreased, or a notification, such as a warning or other notification, can be delivered.

FIG. 1 illustrates generally an example of a system 100 including an implantable medical device 105. The implantable medical device 105 generally includes a first energy delivery circuit 110, a first electric field detector 115, a second electric field detector 120, and a controller 125. In certain examples, the controller 125 can be an implantable component external to the implantable medical device 105, an external component, or a combination or permutation of an implantable component and an external component. In other examples, some or all of the functionality of the first energy delivery circuit 110, the first electric field detector 115, or the second electric field detector 120, can be implemented using the controller 125.

In this example, the first energy delivery circuit 110 can be configured to deliver a first energy to a first thoracic location of a subject. In an example, the first energy delivery circuit 110 can be configured to deliver a nondefibrillating or nonfibrillation-inducing energy to the subject. In other examples, other energies can be configured to be delivered to the subject, such as a defibrillating energy, a fibrillation-inducing energy, a pacing energy, or other energy configured to be delivered to the subject. In an example, the first energy delivery circuit 110 can include at least one of a voltage source and a current source. In certain examples, the first energy delivery circuit 110 can include a bradycardia pacemaker, a cardiac resynchronization therapy (CRT) device, an antitachycardia pacemaker, a cardioverter, a defibrillator, a combination pacemaker/defibrillator, a drug delivery device, or other implantable or external device capable of delivering an energy to the subject.

In an example, the first thoracic location can include one or more than one thoracic location. The first thoracic location can include at least one thoracic location in, on, or near a first chamber of a heart, such as at least one of a right ventricle of the heart, a right atrium of the heart, a superior vena cava, an internal pectoral region of the thorax, and an internal abdominal region. In other examples, the first thoracic location can include any location capable of receiving energy from the first energy delivery circuit 110, such as an external thoracic location or other thoracic location capable of receiving energy.

In the example of FIG. 1, the first electric field detector 115 can be configured to detect a first electric field at a second thoracic location. In an example, the first electric field can include the electric field generated from the delivered first energy from the first energy delivery circuit 110. In an example, the second thoracic location can include one or more than one thoracic location. The second thoracic location can include a target region of the heart. Generally, the target region of the heart can be considered to be the region of the heart having the weakest electric field intensity in response to a delivered energy. In this example, the target region of the heart can be considered to be the region of the heart having the weakest electric field intensity in response to the delivered first energy. In an example, the second thoracic location can include one or more locations in, on, or near at least one of an apical region of the heart and a lateral wall of the heart, such as in, on, or near at least one of a left apical region of the heart and a left ventricular free lateral wall of the heart.

In an example, the second electric field detector 120 can be configured to detect a second electric field between a third thoracic location and a fourth thoracic location. The third thoracic location can include one or more than one thoracic location at or near the first thoracic location, such as at or near the right ventricle of the heart. The fourth thoracic location can include one or more than one thoracic location at or near the second thoracic location, such as at or near the target region of the heart, e.g., in, on, or near at least one of a left apical region of the heart and a left ventricular free lateral wall of the heart. In an example, the detected second electric field can be indicative of the distance between the third thoracic location and the fourth thoracic location. Or, the detected second electric field can be used to accommodate distance variation between the third thoracic location and the fourth thoracic location.

In an example, the first electric field detector 115 can include the second electric field detector 120, or the second electric field detector 120 can include the first electric field detector 115.

In the example of FIG. 1, the controller 125 can be communicatively coupled to the first energy delivery circuit 110, the first electric field detector 115, and the second electric field detector 120. In certain examples, the controller 125 can be configured to send information to, or to receive information from, the first energy delivery circuit 110. Such information can include the amplitude, magnitude, or value of the delivered first energy. The controller 125 can also be configured to send information to, or receive information from, the first electric field detector 115. Such information can include the electric field detected at the second thoracic location. The controller 125 can also be configured to send information to, or receive information from, the second electric field detector 120. Such information can include the electric field detected between the third thoracic location and the fourth thoracic location.

Generally, the controller 125 can be configured to calculate an estimated defibrillation threshold using the information sent to, or received from, the first energy delivery circuit 110. Such information can include information about the non-defibrillating or nonfibrillation-inducing delivered first energy delivered. The estimated defibrillation threshold calculation can also use the information received from the first electric field detector 115. Such information can include information about the detected first electric field. The estimated defibrillation threshold calculation can also use the information received from the second electric field detector 120. Such information can include information about the detected second electric field. The estimated defibrillation threshold can be thought of as the estimated threshold amount of energy needed to terminate a fibrillation.

In an example, the controller 125 can be configured to calculate an estimated defibrillation threshold, such as a first estimated defibrillation threshold, using the information sent to, or received from, the first energy delivery circuit 110. Such information can include information about the nondefibrillating or nonfibrillation-inducing delivered first energy. The estimated defibrillation threshold can also be calculated using the information received from the first electric field detector 115. Such information can include information about the electric field detected at the second thoracic location. In another example, the controller 125 can be configured to calculate an adjusted estimated defibrillation threshold, such as by using an estimated defibrillation threshold and the information received from the second electric field detector 120, such as the electric field detected between the third thoracic location and the fourth thoracic location.

In other examples, the controller 125 can be configured to detect a change in at least one value. The at least one value can include at least one of an estimated defibrillation threshold, information from the first electric field detector 115 (e.g., the detected first electric field), and information from the second electric field detector 120 (e.g., the detected second electric field). Generally, detecting a change in the at least one value can be used to detect a change in the estimated defibrillation threshold. It can also be used to detect a change in the estimated defibrillation threshold without calculating or recalculating the estimated defibrillation threshold, such as by detecting a change in the detected first electric field, detecting a change in the detected second electric field, etc. A change in the estimated defibrillation threshold, a change in the detected first electric field, a change in the detected second electric field, etc., can be indicative of a subject condition change, a system configuration change (e.g., electrode or lead tissue build-up, electrode or lead dislodgment, electrode or lead failure, other circuitry failure, etc.), or other change. In an example, the change in the at least one value can be detected by comparing the at least one value to a different value, such as a specified value (e.g., a specified threshold, an absolute threshold, a device specific threshold, a safety-margin threshold, etc.), baseline, or previous or subsequent information about the at least one value.

Figure 2:
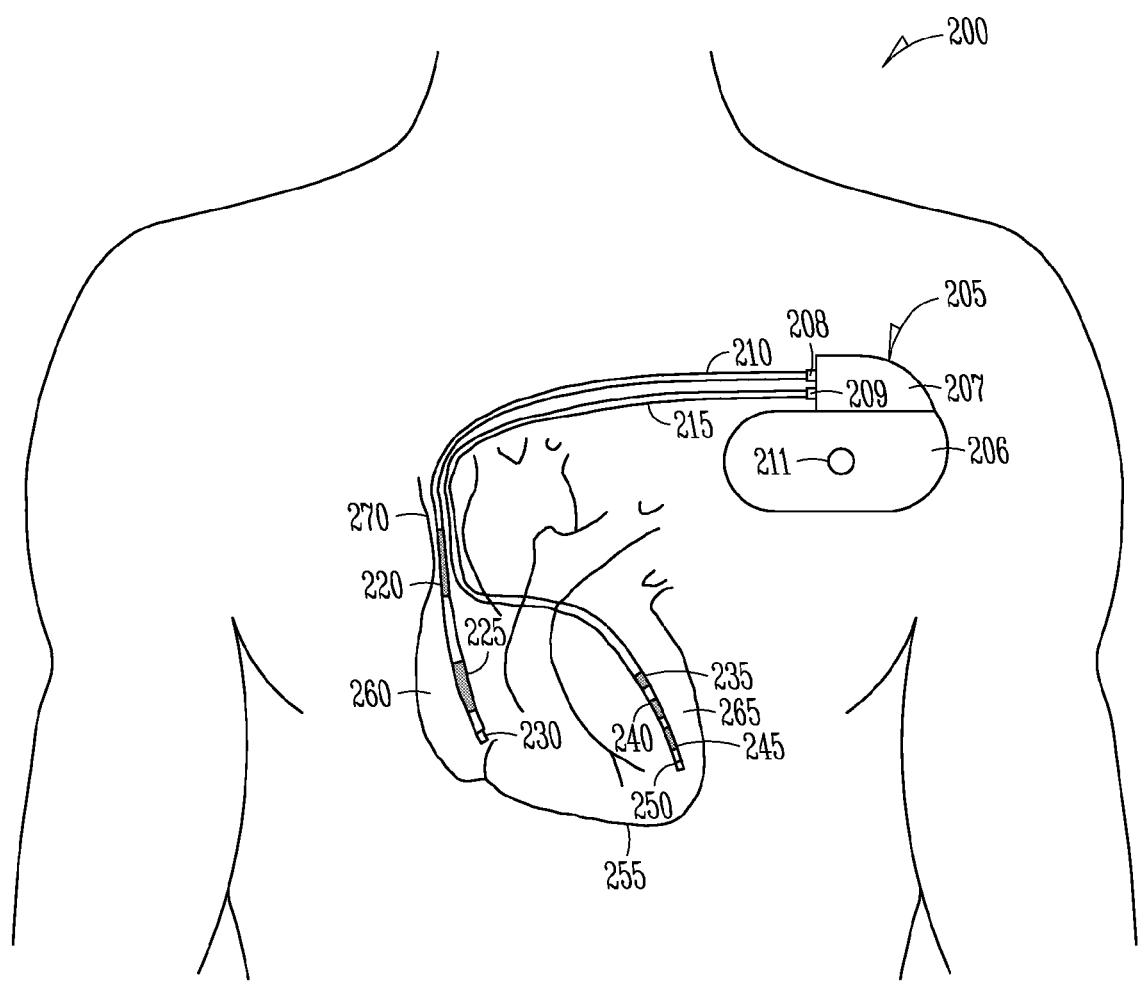
FIG. 2 illustrates generally an example of portions of a system including an implantable device, a first terminal, the first terminal coupled to a first lead, the first lead having multiple electrodes, and a second terminal, the second terminal coupled to a second lead, the second lead having multiple electrodes.

FIG. 2 illustrates generally an example of portions of a system 200 including an implantable medical device 205, a first lead 210, a second lead 215, and a heart 255. The implantable medical device 205 can include a housing 206, a header 207, a "can" electrode 211, a first terminal 208 configured to couple the first lead 210 to the implantable medical device 205, and a second terminal 209 configured to couple the second lead 215 to the implantable medical device 205. The first lead 210 can include a first electrode 220 configured to be located in the super vena cava 270 of the heart 255, a second electrode 225 configured to be located in the right ventricle 260 of the heart 255, and a third electrode 230 configured to be located in the right ventricle 260. The second lead 215 can include a fourth electrode 235 configured to be located in the left ventricle 265 of the heart 255, a fifth electrode 240 configured to be located in the left ventricle 265, a sixth electrode 245 configured to be located in the left ventricle 265, and a seventh electrode 250 configured to be located in the left ventricle 265.

In an example, the implantable medical device 205 can include a cardiac rhythm management device. The implantable medical device 205 can include the first energy delivery circuit 110, the first electric field detector 115, the second electric field detector 120, or the controller 125.

In an example, the implantable medical device 205 can include a housing 206. Generally, the exterior of the housing 206 (also referred to as a "case" or "can") can include a conductive metal, such as titanium. In an example, the housing 206 can act as an electrode (e.g., a "can" electrode 211).

In an example, the implantable medical device 205 can include a header 207. Generally, the header 207 can be formed using an insulative material, such as molded plastic. The header 207 can include at least one receptacle, such as the first terminal 208 or the second terminal 209, to receive at least one lead, such as the first lead 210 or the second lead 215. In an example, the header 207 can also include an electrode, such as an indifferent electrode. In certain examples, an electrode located on the implantable medical device 205, such as the "can" electrode 211 or the indifferent electrode, can be electrically connected to another electrode from the system 200, e.g., the first electrode 220, the second electrode 225, etc.

In an example, the first lead 210 or the second lead 215 can be configured to couple, such as electrically couple, the implantable medical device 205 to at least one thoracic location, such as the first thoracic location, the second thoracic location, the third thoracic location, or other thoracic location. In an example, the first lead 210 or the second lead 215 can be configured to be located in at least a portion of the heart 255.

In an example, the first lead 210 can be configured to electrically connect the implantable medical device 205 to the super vena cava 270, the right atrium, or the right ventricle 260 using at least one electrode, such as the first electrode 220, the second electrode 225, or the third electrode 230. In certain examples, the first lead 210 can electrically connect the implantable medical device 205 to the super vena cava 270 or the right atrium using the first electrode 220, or to the right ventricle using the second electrode 225 or the third electrode 230. In certain examples, the first electrode 220 or the second electrode 225 can include a coil-type electrode. In an example, the coil type electrode can have a macroscopic surface area approximately between 2 square centimeters and 20 square centimeters. In certain examples, the third electrode 230 can include a tip electrode, or the third electrode 230 can be configured to be disposed at the apex of the right ventricle 260. In an example, one or more than one electrode, such as the first electrode 220, the second electrode 225, or the third electrode 230, can be electrically connected or can be configured to operate independently.

In an example, the second lead 215 can be configured to electrically connect the implantable medical device 205 to the left ventricle 265 using at least one electrode, such as the fourth electrode 235, the fifth electrode 240, the sixth electrode 245, or the seventh electrode 250. In certain examples, the fourth electrode 235, the fifth electrode 240, the sixth electrode 245, or the seventh electrode 250 can be sized or shaped for implementation in or on the left region of the heart, such as in or on the left apical region or the left ventricular free lateral wall or the left posterior region of the heart 255. In an example, the seventh electrode 250 can include a tip electrode. In certain examples, the seventh electrode 250 can be configured to be disposed at the apex of the left ventricle 265 or at or near the left ventricular free lateral wall of the heart 255. In an example, one or more than one electrode, such as the fourth electrode 235, the fifth electrode 240, the sixth electrode 245, or the seventh electrode 250, can be electrically connected or can be configured to operate independently.

Figure 3:
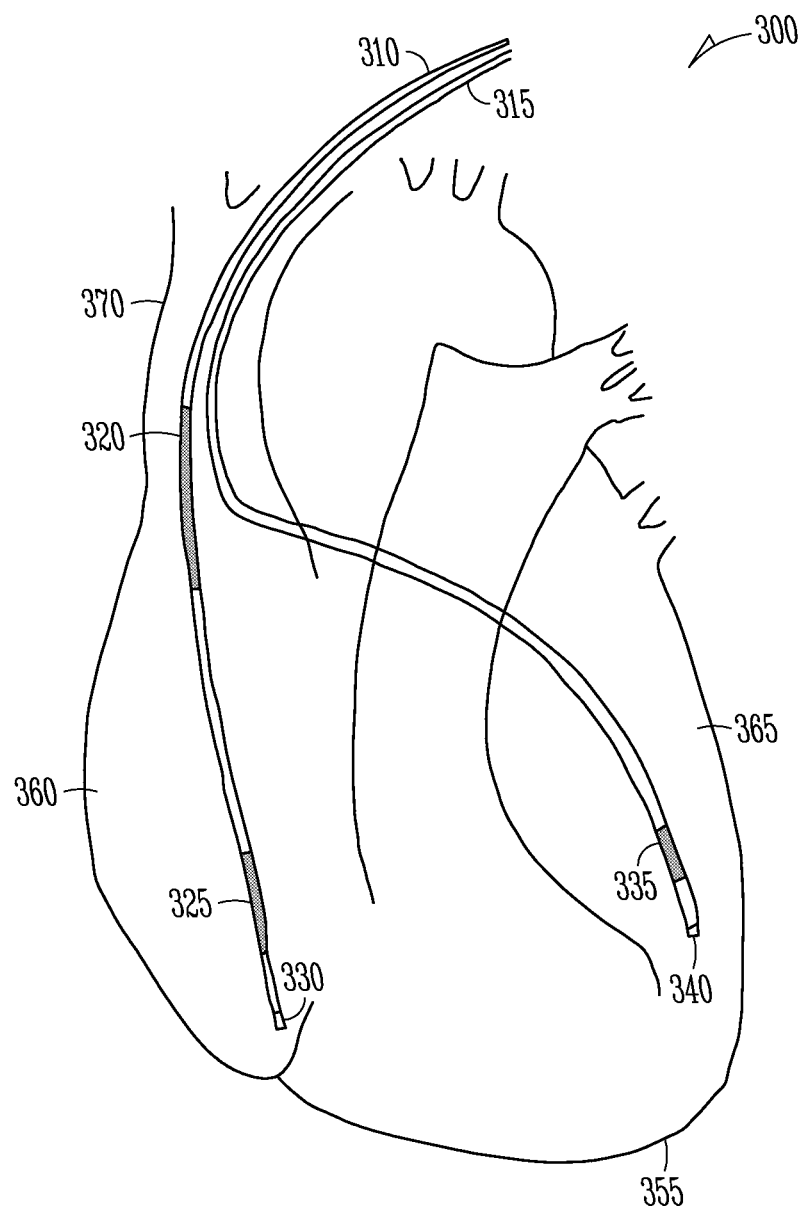
FIG. 3 illustrates generally an example of portions of a system including a first lead, the first lead having multiple electrodes, and a second lead, the second lead having multiple electrodes.

FIG. 3 illustrates generally an example of portions of a system 300 including a first lead 310, a second lead 315, and a heart 355. The first lead 310 can include a first electrode 320 configured to be located in the super vena cava 370, a second electrode 325 configured to be located in the RV 360, and a third electrode 330 configured to be located in the RV 360. The second lead can include a fourth electrode 335 configured to be located in the LV 365 and a fifth electrode 340 configured to be located in the LV 365. Generally, the second lead 315 can be configured to be located in, on, or near a left apical region of the heart or a left ventricular free lateral wall of the heart.

Figure 4:
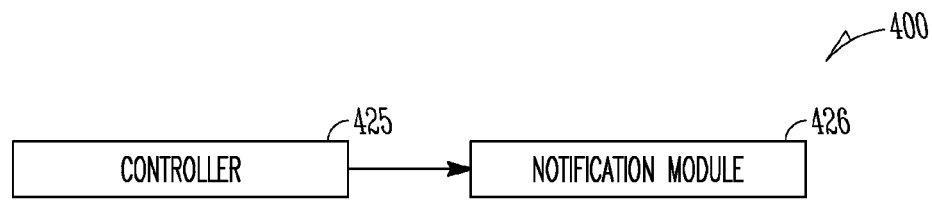
FIG. 4 illustrates generally an example of portions of a system including a controller and a notification module.

FIG. 4 illustrates generally an example of portions of a system 400 including a controller 425 and a notification module 426. In an example, some or all of the functionality of the notification module 426 can be implemented in the controller 425.

In an example, the notification module 426 can be communicatively coupled to the controller 425. The notification module 426 can be configured to send information to, or to receive information from, the controller 425. Such information can include the estimated defibrillation threshold, information from the first electric field detector 115, information from the second electric field detector 120, etc. In an example, the notification module 426 can be configured to communicate information from the controller 425, or other component, e.g., the first electric field detector 115, the second electric field detector 120, etc., to a user, to a subject, or to another device, such as an external programmer. In an example, the notification module 426 can be configured to communicate with a remote data server or a user interface (e.g., such as a LATITUDE or other patient management system with a remote user interface). In another example, the notification module 426 can be configured to communicate to an external device, such as an external repeater or a remote server, which can be configured to communicate, such as by an e-mail or other communication, to the user. In another example, a notification, such as audible notification (e.g., a buzz, bell, or other sound) or mechanical notification (e.g., a vibration), can be used to notify the subject.

Figure 5:
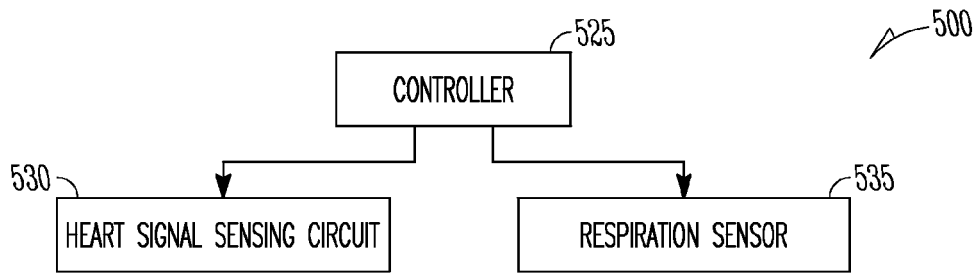
FIG. 5 illustrates generally an example of portions of a system including a controller, a heart signal sensing circuit, and a respiration sensor.

FIG. 5 illustrates generally an example of portions of a system 500 including a controller 525, a heart signal sensing circuit 530, and a respiration sensor 535. In certain examples, some or all of the functionality of the heart signal sensing circuit 530 or the respiration sensor 535 can be implemented in the controller 525.

In certain examples, an energy delivery circuit, such as the first energy delivery circuit 110, can be configured to deliver an energy at a specified portion of the heart signal, such as at the end of diastole or other portion of the heart signal, or at a specified portion of the respiration signal, such as at the transition from inspiration to expiration or other portion of the respiration signal, including an average respiration signal, using a controller, such as the controller 525.

In this example, the heart signal sensing circuit 530 can be configured to sense a heart signal of a subject. The heart signal can include any signal indicative of the electrical or mechanical cardiac activity of the heart, e.g., an electrocardiogram ("ECG") signal, an impedance signal, an acceleration signal, etc. The heart signal sensing circuit 530 can be configured to produce an encoded representation of a heart signal, such as an electrically or optically encoded heart signal, that includes information about the actual heart signal of the subject. The heart signal sensing circuit 530 can include any device configured to sense the cardiac activity of the subject. In certain examples, the heart signal sensing circuit 530 can include a cardiac signal sensor, such as one or more than one electrode or lead configured to sense one or more than one depolarization, or an impedance sensor or a mechanical sensor, such as an accelerometer, to sense one or more than one contraction.

In an example, the respiration sensor 535 can be configured to sense a respiration signal of the subject. The respiration signal can include any signal indicative of the respiration of the subject, such as inspiration, expiration, or any combination, permutation, or component of the respiration of the subject. The respiration sensor 535 can be configured to produce a respiration signal, such as an electrical or optical respiration signal, that includes information about the respiration of the subject. In certain examples, the respiration sensor 535 can include an implantable sensor including at least one of an accelerometer, an impedance sensor, and a pressure sensor.

In an example, the respiration sensor 535 can include an accelerometer configured to sense an acceleration signal indicative of a cyclical variation indicative of respiration, such as that disclosed in the commonly assigned Kadhiresan et al. U.S. Pat. No. 5,974,340 entitled "APPARATUS AND METHOD FOR MONITORING REPSIRATORY FUNCTION IN HEART FAILURE PATIENTS TO DETERMINE EFFICACY OF THERAPY," (herein "Kadhiresan et al. '340") which is hereby incorporated by reference in its entirety, including its disclosure of using an accelerometer to detect respiration. In another example, the respiration sensor 535 can include a vibration sensor, such as that disclosed in the commonly assigned Hatlestad et al. U.S. Pat. No. 6,949,075 entitled "APPARATUS AND METHOD FOR DETECTING LUNG SOUNDS USING AN IMPLANTED DEVICE," (herein "Hatlestad et al. '075") which is hereby incorporated by reference in its entirety, including its disclosure of using a vibration sensor to detect respiration. In other examples, other accelerometer configurations can be used to sense the respiration signal.

In another example, the respiration sensor 535 can include an impedance sensor configured to sense an impedance signal indicative of respiration, such as that disclosed in the commonly assigned Kadhiresan et al. '340, incorporated by reference in its entirety. In another example, the respiration sensor 535 can include a transthoracic impedance sensor, such as that disclosed in the commonly assigned Hartley et al. U.S. Pat. No. 6,076,015 entitled "RATE ADAPTIVE CARDIAC RHYTHM MANAGEMENT DEVICE USING TRANSTHORACIC IMPEDANCE," which is hereby incorporated by reference in its entirety, including its disclosure of using a thoracic impedance sensor to detect respiration. In other examples, other impedance sensor configurations can be used to sense the respiration signal.

In another example, the respiration sensor 535 can include a pressure sensor configured to sense a pressure signal indicative of respiration, such as that disclosed in the commonly assigned Hatlestad et al. '075, incorporated by reference in its entirety, including its disclosure of sensing a pressure signal indicative of respiration. In other examples, other pressure sensor configurations, such as a pulmonary artery pressure sensor, a ventricular pressure sensor, a thoracic pressure sensor, etc., can be used to sense a respiration signal.

In the example of FIG. 5, the controller 525 can be communicatively coupled to the heart signal sensing circuit 530 and the respiration sensor 535. In certain examples, the controller 525 can be configured to receive information from the heart signal sensing circuit 530, such as the heart signal, or the controller 525 can be configured to receive information from the respiration sensor 535, such as the respiration signal.

In an example, the controller 525 can be configured to detect at least one portion of the heart signal using information from the heart signal sensing circuit 530. Typically, the at least one portion of the heart signal feature can include at least one feature or component of an ECG signal, e.g., at least one feature or component of a P-wave, at least one feature or component of a Q-wave, at least one feature or component of a R-wave, at least one feature or component of a S-wave, at least one feature or component of a R-wave, or any combination or permutation of features or components of the ECG signal, or any mechanical cardiac features of a pressure signal, an impedance signal, or an acceleration signal indicative of the cardiac activity of the subject.

In an example, the controller 525 can be configured to detect at least one portion of at least one phase of the respiration signal using information from the respiration sensor 535. In certain examples, the at least one portion of the at least one phase of the respiration signal can include at least one portion of at least one of an inspiration, an expiration, a transition between inspiration and expiration, and a transition between expiration and inspiration.

In an example, the controller 525 can be configured to send information, such as information from the heart signal, e.g., the at least one feature or component of the R-wave, or information from the respiration signal, e.g., the at least one portion of an inspiration, to the first energy delivery circuit 110. In another example, the controller 525 can be configured to send information, such as information from the heart signal, e.g., the at least one feature of component of the R-wave, or information from the respiration signal, e.g., the at least one portion of an inspiration, to the first electric field detector 115 or the second electric field detector 120.

In other examples, an energy detector, such as the first electric field detector 115 or the second electric field detector 120, can be configured to sense an energy, such as an electric field at the second thoracic location or an electric field between the third thoracic location and the fourth thoracic location, at a specified portion of the heart signal, such as at the end of diastole or other portion of the heart signal, or at a specified portion of the respiration signal, such as at the transition from inspiration to expiration or other portion of the respiration signal, using a controller, such as the controller 525. Generally, sensing information at a specified portion of the heart signal or the respiration signal can reduce variation otherwise present due to heart activity or respiration activity.

Figure 6:
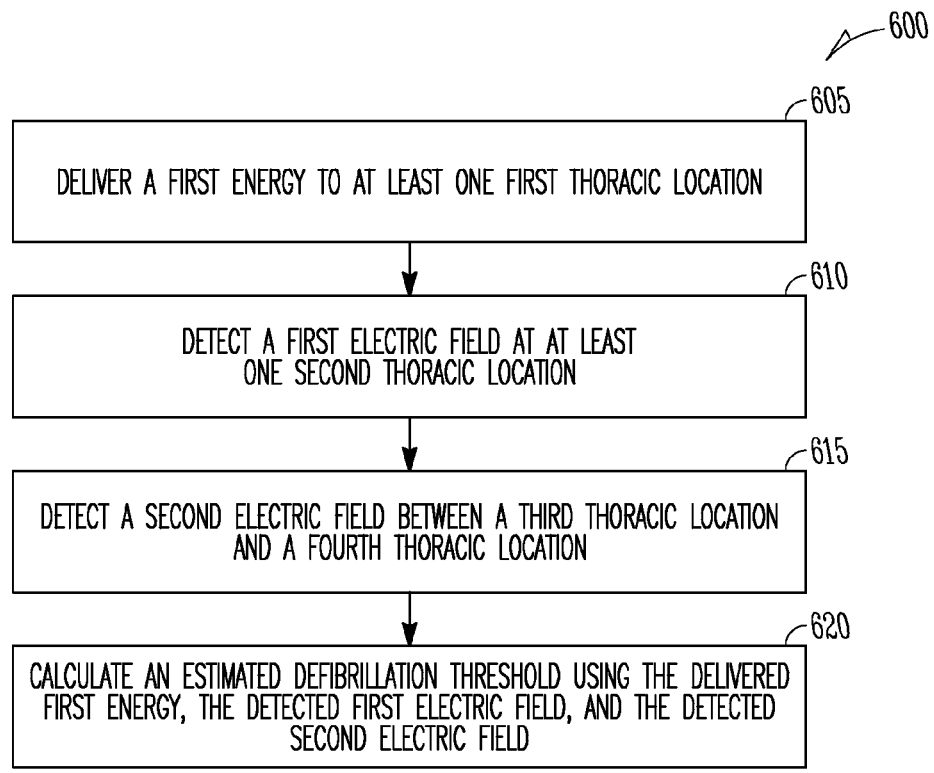
FIG. 6 illustrates generally an example of a method including delivering a first energy to at least one first thoracic location, detecting a first electric field at least one second thoracic location, and detecting a second electric field between a third thoracic location and a fourth thoracic location. The method further includes calculating an estimated defibrillation threshold using the delivered first energy, the detected first electric field, and the detected second electric field.

FIG. 6 illustrates generally an example of a method 600 including delivering a first energy to at least one first thoracic location, detecting a first electric field at least one second thoracic location, and detecting a second electric field between a third thoracic location and a fourth thoracic location. The method 600 further includes calculating an estimated defibrillation threshold using the delivered first energy, the detected first electric field, and the detected second electric field.

At 605, a first energy can be delivered to at least one first thoracic location. In an example, the first energy can be delivered using the first energy delivery circuit 110.

In an example, at 605, the first energy can be delivered to the first thoracic location using the first lead 210. In an example, the first energy can be delivered using the first electrode 220 and the second electrode 225, such as by delivering the first energy between the first electrode 220 and the second electrode 225. In other examples, other leads, electrodes, or devices can be used to deliver the first energy to the at least one first thoracic location.

At 610, a first electric field can be detected at least one second thoracic location. In an example, the first electric field can include the electric field generated from the delivered first energy from the first energy delivery circuit 110. In an example, the first electric field can be detected using the first electric field detector 115.

In an example, at 610, the first electric field can be detected at the second thoracic location using the second lead 215. In an example, the first electric field can be detected using at least one electrode, such as by detecting the electric field between the fourth electrode 235 and the fifth electrode 240. In other examples, other electrodes, such as the sixth electrode 245 or the seventh electrode 250, or a combination of multiple electrodes (e.g., two or more electric fields detected using three or more electrodes synthesized to be indicative of the first electric field) can be used to detect the first electric field.

At 615, a second electric field can be detected between a third thoracic location and a fourth thoracic location. In an example, the second electric field can include the electric field generated from the delivered first energy from the first energy delivery circuit 110. In an example, the second electric field can be detected using the second electric field detector 120.

In an example, at 615, the second electric field can be detected using at least one electrode located at or near the third thoracic location and at least one electrode located at or near the fourth thoracic location, such as by detecting the electric field between the third electrode 230 and the seventh electrode 250.

In other examples, the second electric field can include the electric field generated from other delivered energy, such as a second energy delivered from a second energy delivery circuit. In an example, the first energy delivery circuit 110 can include the second energy delivery circuit. In other examples, the second energy can be delivered separately from the first energy, such as by using a separate device, or by delivering the second energy at a separate time than the first energy.

In an example, the second electric field can include an electric field detected between a RV electrode and a LV electrode, or $V_{LV\text{-}RV}$. In an example, the $V_{LV\text{-}RV}$ can be detected using the third electrode 230 and the seventh electrode 250.

Generally, the estimation error ("$V_{err}$") is the error between a shock-determined defibrillation threshold, or other known or established defibrillation threshold ("$VDFT_{real}$"), and an estimated defibrillation threshold ("$VDFT_{est}$"). The $V_{err}$ can be defined as a ratio of the difference between the $VDFT_{est}$ and the $VDFT_{real}$ over the $VDFT_{real}$:

$$V_{err} = \frac{(VDFT_{est} - VDFT_{real})}{VDFT_{real}}.$$

The present inventor has recognized, among other things, that the $V_{err}$ generally correlates to the electric field detected between the third thoracic location and the fourth thoracic location, such as $V_{LV\text{-}RV}$. Generally, the second electric field decreases as the distance between the third thoracic location and the fourth thoracic location decreases. The distance between the third thoracic location and the fourth thoracic location can be indicative of the location of the a lead in the LV, such as the second lead 215. In an example, a decrease in the second electric field can be indicative of an increase in the distance between the LV lead and the target region of the heart. As the distance between the LV lead and the target region of the heart increases, the $VDFT_{est}$ can be underestimated. Thus, the second electric field can be used to accurately estimate a defibrillation threshold.

At 620, an estimated defibrillation threshold can be calculated using the delivered first energy, the detected first electric field, and the detected second electric field. In an example, the estimated defibrillation threshold can be calculated using the controller 125.

In an example, the estimated defibrillation threshold can include a first estimated defibrillation threshold ("$VDFT1_{est}$"). In an example, at 620, the $VDFT1_{est}$ can be calculated by multiplying the delivered first energy ("$V_1$") by a ratio of the desired, or "target", electric field strength ("A"), and the detected first electric field ("$V_2$"), such as the gradient of the detected first electric field, and then multiplying that result by a function of the electric field detected between the third thoracic location and the fourth thoracic location ("$V_{3\text{-}4}$"):

$$VDFT1_{est} = V_1 \frac{A}{\nabla V_2} \frac{1}{(aV_{3\text{-}4} + b + 1)}.$$

In this example, the $V_{3\text{-}4}$ is generally correlated to a defibrillation threshold estimation error.

Generally, the desired, or "target", electric field strength is the value of the minimal potential gradient for a successful defibrillation. In an illustrative example, the desired electric field strength can be 5 volts/cm. In other examples, the desired electric field strength can be selected at any desired value, which will generally be capable of reliably converting an abnormal heart rhythm to normal heart rhythm. In certain examples, the desired electric field strength can be selected using a target voltage gradient or a target voltage gradient and a safety margin. The safety margin generally includes a margin, such as a 10 joule margin, above the minimum estimated amount of energy required to convert an abnormal heart rhythm to normal heart rhythm. Generally, calculating the estimated defibrillation threshold with the safety margin increases the probability that the calculated defibrillation threshold will produce the desired results.

In this example, a and b are coefficients. The coefficients a and b are generally calculated using a relationship between the $V_{3\text{-}4}$ and a defibrillation threshold estimation error. In certain examples, the coefficients a and b can be calculated individually for each subject, such as by using information from a past defibrillation threshold, the coefficients a and b can be calculated or established for a certain subject population, such as for subjects having a specific condition or related conditions, or for subjects with similar attributes, or the coefficients a and b can be calculated or established for an entire subject population, such as by using information from one or more than one individually calculated coefficient. In other examples, other coefficients can be calculated, including a linear set of at least one coefficient or a nonlinear set of at least one coefficient.

Figure 7:
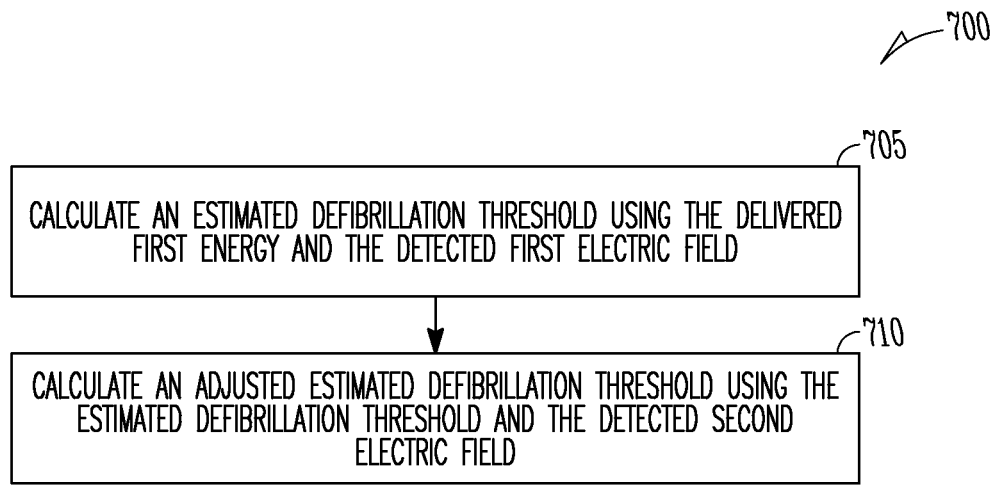
FIG. 7 illustrates generally an example of portions of a method including calculating an estimated defibrillation threshold using the delivered first energy and the detected first electric field. The method further includes calculating an adjusted estimated defibrillation threshold using the estimated defibrillation threshold and the detected second electric field.

FIG. 7 illustrates generally an example of portions of a method 700 including calculating an estimated defibrillation threshold using the delivered first energy and the detected first electric field. The method 700 further includes calculating an adjusted estimated defibrillation threshold using the estimated defibrillation threshold and the detected second electric field.

Generally, the adjusted estimated defibrillation threshold ("$VDFT_{adj}$") allows the controller 125 or other device to adjust the estimated defibrillation threshold using the detected second electric field, without calculating or recalculating the estimated defibrillation threshold.

At 705, an estimated defibrillation threshold can be calculated using the delivered first energy and the detected first electric field. In an example, the estimated defibrillation threshold can be calculated using the controller 125.

In an example, at 705, the estimated defibrillation threshold ("$VDFT_{est}$") can be calculated by multiplying the delivered first energy ("$V_1$") by a ratio of the desired, or "target", electric field strength ("A"), e.g., 5 volts/cm, and the detected first electric field ("$V_2$") such as the gradient of the detected first electric field:

$$VDFT_{est} = V_1 \frac{A}{\nabla V_2}.$$

At 710, an adjusted estimated defibrillation threshold can be calculated using the estimated defibrillation threshold, e.g., the estimated defibrillation threshold calculated at 705, and the detected second electric field.

In an example, at 710, the adjusted estimated defibrillation threshold ("$VDFT_{adj}$") can be calculated by multiplying an estimated defibrillation threshold by a function of the $V_{3-4}$, such as $$\frac{1}{(aV_{3-4} + b + 1)}:$$

$$VDFT_{adj} = VDFT_{est} \frac{1}{(aV_{3-4} + b + 1)}.$$

Figure 8:
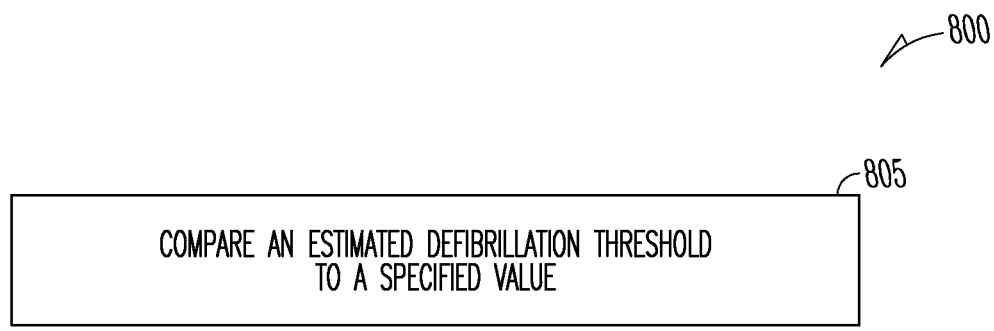
FIG. 8 illustrates generally an example of a portion of a method including comparing an estimated defibrillation threshold to a specified value.

FIG. 8 illustrates generally an example of a portion of a method 800 including comparing an estimated defibrillation threshold to a specified value.

At 805, an estimated defibrillation threshold can be compared to a specified value. In an example, the estimated defibrillation threshold can be compared to the specified value in order to determine if the estimated defibrillation threshold is above or below the specified value, or to determine if the estimated defibrillation threshold has changed. Generally, a change in the estimated defibrillation threshold can be indicative of a subject condition change, a system configuration change (e.g., electrode or lead tissue build-up, electrode or lead dislodgment, electrode or lead failure, other circuitry failure, etc.), or other change.

In other examples, the detected first electric field, the detected second electric field, etc., can be compared to the specific value. The estimated defibrillation threshold can also be compared to the specified value in order to ensure that various components of the systems 100-500, such as the controller 125, the first electric field detector 115, the second electric field detector 120, or other component of systems 100-500, are receiving, delivering, or otherwise being exposed to expected data, expected information, or expected results. In other examples, other datum can be compared to the specified value, such as information about the detected first electric field, information about the detected second electric field, or other information.

In certain examples, the specified value can include a specified threshold, an absolute threshold, a device specific threshold, a safety-margin threshold, baseline, or other specified value.

Figure 9:
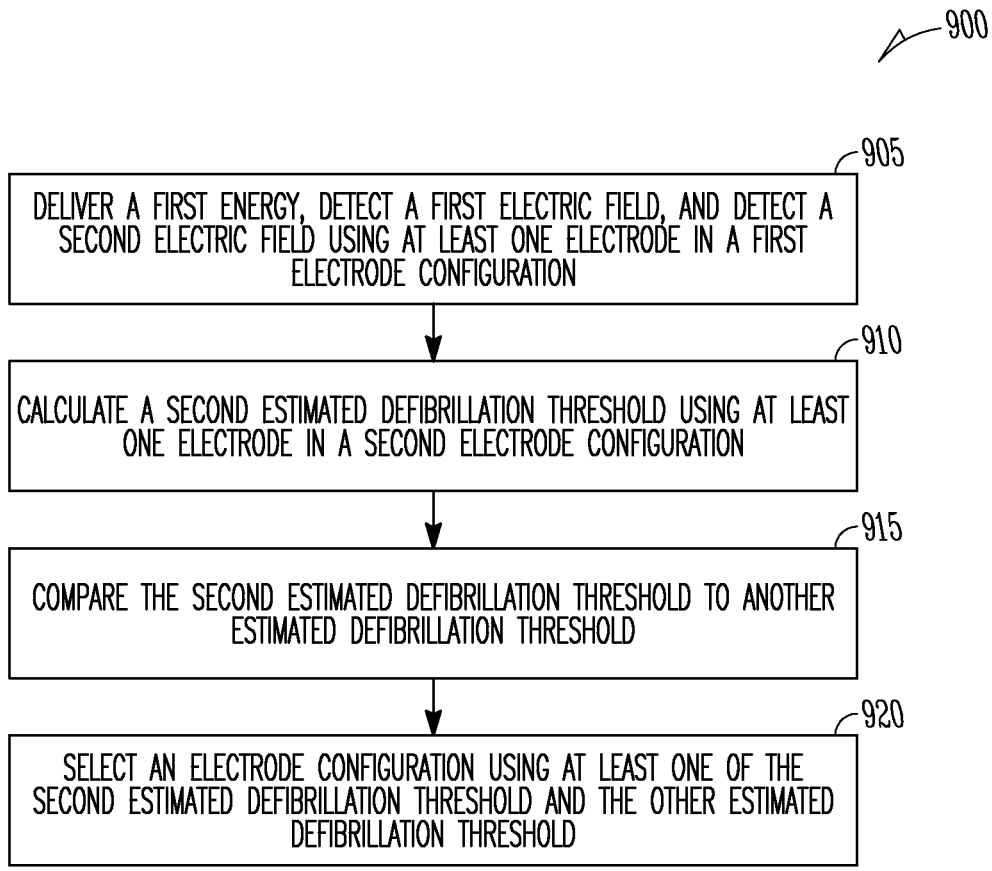
FIG. 9 illustrates generally an example of portions of a method including delivering a first energy, detecting a first electric field, and detecting a second electric field using at least one electrode in a first electrode configuration. The method further includes calculating a second estimated defibrillation threshold using at least one electrode in a second electrode configuration, and comparing the second estimated defibrillation threshold to another estimated defibrillation threshold. The method further includes selecting an electrode configuration using at least one of the second estimated defibrillation threshold and the other estimated defibrillation threshold.

FIG. 9 illustrates generally an example of portions of a method 900 including delivering a first energy, detecting a first electric field, and detecting a second electric field using at least one electrode in a first electrode configuration. The method 900 further includes calculating a second estimated defibrillation threshold using at least one electrode in a second electrode configuration, and comparing the second estimated defibrillation threshold to another estimated defibrillation threshold. The method 900 further includes selecting an electrode configuration using at least one of the second estimated defibrillation threshold and the other estimated defibrillation threshold.

At 905, a first energy can be delivered, a first electric field can be detected, and a second electric field can be detected using at least one electrode in a first electrode configuration. In an example, the first electrode configuration can be selected by the controller 125. In other examples, the first electrode configuration can be selected by a user and communicated to the controller 125 or to the implantable medical device 105.

In an example, at 905, the first energy can be delivered using at least one electrode, such as by using the first electrode 220 and the second electrode 225. The first electric field can be detected using at least one electrode, such as by using the fourth electrode 235 and the fifth electrode 240. The second electric field can be detected using at least one electrode, such as by using the third electrode 230 and the seventh electrode 250. In this example, the first electrode configuration can include the first electrode 220, the second electrode 225, the third electrode 230, the fourth electrode 235, the fifth electrode 240, and the seventh electrode 250. In other examples, the first electrode configuration can include other electrodes, such as the sixth electrode 245, the "can" electrode 211, etc.

At 910, a second estimated defibrillation threshold can be calculated using at least one electrode in a second electrode configuration. Generally, the second electrode configuration includes at least one electrode that is not included in the first electrode configuration. In an example, the second electrode configuration can be selected by the controller 125. In other examples, the second electrode configuration can be selected by a user and communicated to the controller 125 or to the implantable medical device 105.

In an example, at 910, the first energy can be delivered to the first thoracic location, the first electric field can be detected at the second thoracic location, and the second electric field can be detected between the third thoracic location and the fourth thoracic location using the second electrode configuration. In an example, the first electric field can be detected using the fourth electrode 235 and the sixth electrode 245. In this example, the second electrode configuration can include the fourth electrode 235, the sixth electrode 245, and other electrodes.

In an example, at 910, the second estimated defibrillation threshold can be calculated using the second electrode configuration, like the estimated defibrillation threshold calculated at 620. In an example, the second estimated defibrillation threshold can be calculated using the controller 125.

At 915, the second estimated defibrillation threshold can be compared to another estimated defibrillation threshold. Generally, the second estimated defibrillation threshold is compared to the other estimated defibrillation threshold in order to select an electrode configuration. In an example, the other estimated defibrillation threshold can include an estimated defibrillation threshold calculated using the first electrode configuration. In other examples, the other estimated defibrillation threshold can include an expected estimated defibrillation threshold, such as an average, typical, or other estimated or known defibrillation threshold, such as the average of a certain number (e.g., 10) estimated defibrillation thresholds, the average of a certain number (e.g., 5) known defibrillation thresholds, etc. In certain examples, other numbers can be used, or the average, typical, or other threshold can be updated continuously. In an example, the second estimated defibrillation threshold can be compared using the controller 125.

At 920, an electrode configuration can be selected using at least one of the second estimated defibrillation threshold and the other estimated defibrillation threshold. Generally, the electrode configuration yielding the "better" estimated defibrillation threshold (e.g., the closest estimated defibrillation threshold to the expected estimated defibrillation threshold) is preferred. In an example, if one or more than one estimated defibrillation threshold is determined to be invalid (e.g., having an unrealistic result, such as an estimated defibrillation threshold of zero volts), a valid estimated defibrillation threshold is preferred. In certain examples, an invalid estimated defibrillation threshold can include an estimated defibrillation threshold above an upper threshold (e.g., a specified upper threshold), a device-specific threshold (e.g., a device specific safety margin or other threshold), or an estimated defibrillation threshold below a lower threshold (e.g., a specified minimum threshold).

In other examples, a user can select an estimated defibrillation threshold, or notification of an estimated defibrillation threshold, such as an estimated defibrillation threshold above or below a certain threshold, can be provided to the user, such as by using the notification module 426.

Figure 10:
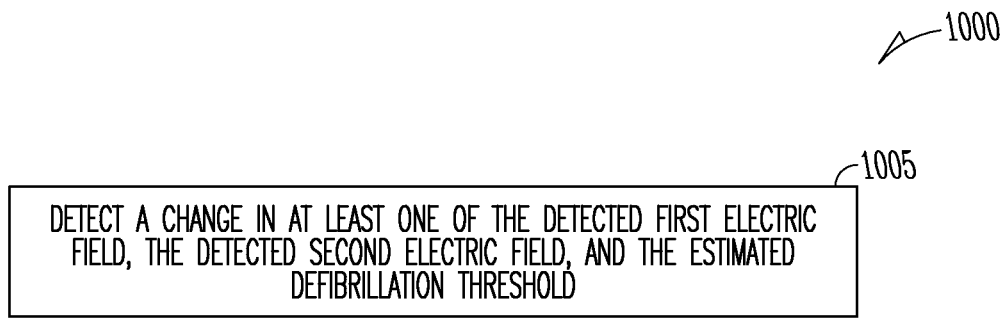
FIG. 10 illustrates generally an example of a portion of a method including detecting a change in at least one of the detected first electric field, the detected second electric field, and the estimated defibrillation threshold.

FIG. 10 illustrates generally an example of a portion of a method 1000 including detecting a change in at least one of the detected first electric field, the detected second electric field, and the estimated defibrillation threshold.

Generally, defibrillation thresholds can change over time. In certain examples, the detected first electric field, the detected second electric field, or the estimated defibrillation threshold can change due to various factors including lead migration, heart size change, or other reasons. In an example, one or more such changes can be detected, such as by using the controller 125.

At 1005, the change in at least one of the detected first electric field, the detected second electric field, and the estimated defibrillation threshold can be detected.

In an example, at 1005, the detected first electric field or the detected second electric field can be compared to at least one previously detected value to detect a change in value. In other examples, the detected first electric field or the detected second electric field can be compared (such as by using the controller 125) to a patient-specific or population-derived historical baseline, to one or more other templates.

In an example, at 1005, the estimated defibrillation threshold can be compared to a previously estimated value to detect a change in value. In other examples, the estimated defibrillation threshold can be compared to a baseline, such as a baseline established using a history of the estimated defibrillation threshold of the subject, of another subject, or of a population, or the estimated defibrillation threshold can be compared to other templates. In an example, the estimated defibrillation threshold can be compared using the controller 125.

FIG. 11 illustrates generally an example of a portion of a method 1100 including providing a notification using information about at least one estimated defibrillation threshold or a detected electric field. In an example, the notification can be provided using the notification module 426.

At 1105, a notification can be provided using information about at least one estimated defibrillation threshold or a detected electric field. In an example, the at least one estimated defibrillation threshold can include the adjusted estimated defibrillation threshold or another estimated defibrillation threshold. In certain examples, the notification can include the value of an estimated defibrillation threshold, the notification can include the results of comparing an estimated defibrillation threshold to a specified value, or the notification can include other information. In an example, the detected electric field can include a detected first electric field or a detected second electric field. In an example, the notification can include a change in a detected electric field. A slow or consistent change in a detected electric field can be indicative of a patient-condition change (e.g., the change occurring over a long period of time, such as days, weeks, or months). A fast or abrupt change in a detected electric field can be indicative of other conditions, such as lead dislodgment (e.g., the change occurring over a short period of time, such as seconds). In an example, the notification can be provided to a subject or a user. In other examples, other information, such as information from the controller 125 or other component, can be provided.

FIG. 12 illustrates generally an example of portions of a method 1200 including sensing at least one of a heart signal and a respiration signal. The method 1200 further includes delivering a first energy at a specified portion of at least one of the heart signal and the respiration signal. In an example, the energy delivery can be enabled using the controller 125.

At 1205, at least one of a heart signal and a respiration signal can be sensed. The heart signal can include any signal indicative of the electrical or mechanical cardiac activity of a heart. In an example, the cardiac signal can be sensed using the heart signal sensing circuit 530. The respiration signal can include any signal indicative of the respiration of a subject, such as inspiration, expiration, or any combination, permutation, or component of the respiration of the subject. In an example, the respiration signal can be sensed using the respiration sensor 535.

At 1210, a first energy can be delivered at a specified portion of at least one of the heart signal of the heart and the respiration signal. In an example, the first energy can be delivered at a specified portion of the heart signal, such as at the end of diastole or other portion of the heart signal, using the first energy delivery circuit 110 or other energy delivery circuit. In an example, at 1210, the first energy can be delivered at a specified portion of the respiration signal, such as at the transition from inspiration to expiration or other portion of the respiration signal, using the first energy delivery circuit 110 or other energy delivery circuit.

FIG. 13 illustrates generally an example of portions of a method 1300 including sensing at least one of a heart signal and a respiration signal. The method 1300 further includes detecting a first electric field or a second electric field at a specified portion of at least one of the heart signal and the respiration signal.

Generally, the method 1300 can enable cardiac-synchronous or respiration-synchronous defibrillation threshold determination by enabling electric field detection at a specified portion of at least one of the heart signal and the respiration signal. In an example, the electric field detection can be enabled using the controller 125.

At 1305, at least one of a heart signal and a respiration signal can be sensed. The heart signal can include any signal indicative of the electrical or mechanical cardiac activity of a heart. In an example, the heart signal can be sensed using the heart signal sensing circuit 530. The respiration signal can include any signal indicative of the respiration of a subject, such as inspiration, expiration, or any combination, permutation, or component of the respiration of the subject. In an example, the respiration signal can be sensed using the respiration sensor 535.

At 1310, a first electric field or a second electric field can be detected at a specified portion of at least one of the heart signal and the respiration signal. In an example, the first electric field or the second electric field can be detected at a specified portion of the heart signal of the heart, such as at the end of diastole or other portion of the heart signal, using the first electric field detector 115 or the second electric field detector 120. In an example, the first electric field or the second electric field can be detected at a specified portion of the respiration signal, such as at the transition from inspiration to expiration or other portion of the respiration signal, using the first electric field detector 115 or the second electric field detector 120.

Figure 14:
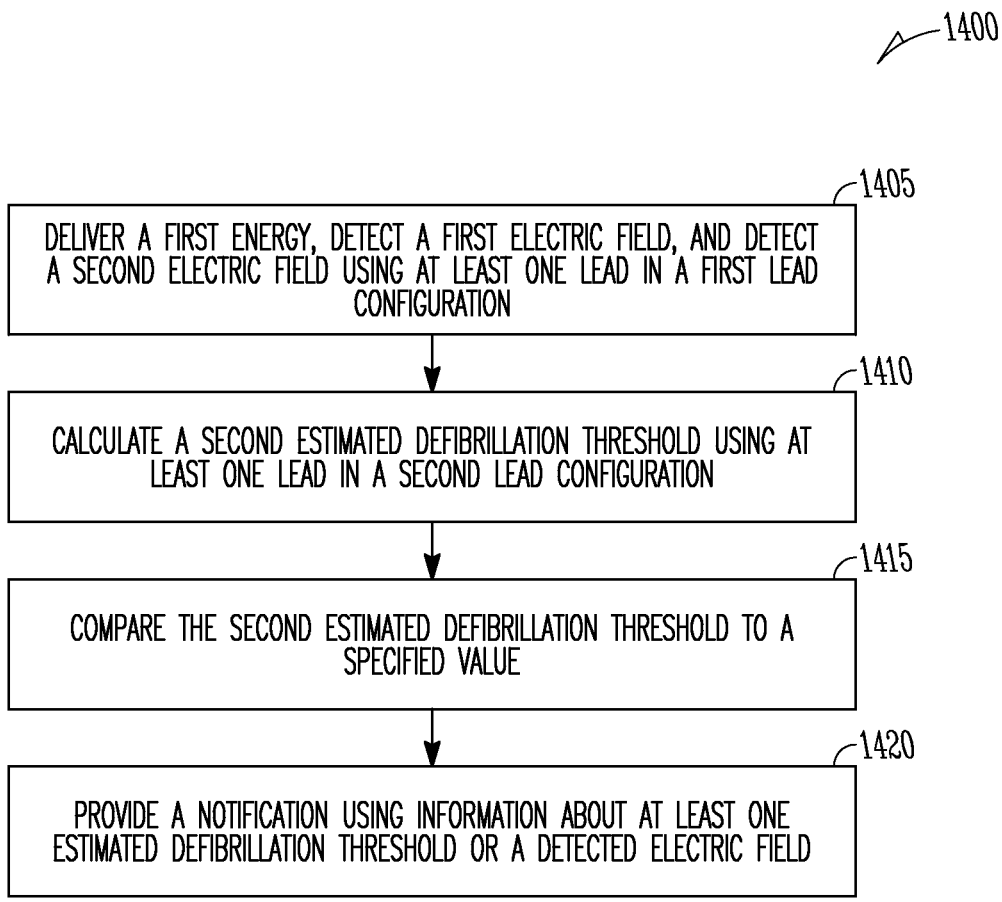
FIG. 14 illustrates generally an example of portions of a method including delivering a first energy, detecting a first electric field, and detecting a second electric field between using at least one lead in a first lead configuration. The method further includes calculating a second estimated defibrillation threshold using at least one lead in a second lead configuration, and comparing the second estimated defibrillation threshold to a specified value. The method further includes providing a notification using information about at least one estimated defibrillation threshold or a detected electric field.

FIG. 14 illustrates generally an example of portions of a method 1400 including delivering a first energy, detecting a first electric field, and detecting a second electric field between using at least one lead in a first lead configuration. The method 1400 further includes calculating a second estimated defibrillation threshold using at least one lead in a second lead configuration, and comparing the second estimated defibrillation threshold to a specified value. The method 1400 further includes providing a notification using information about at least one estimated defibrillation threshold or a detected electric field.

At 1405, a first energy can be delivered, a first electric field can be detected, and a second electric field can be detected using at least one lead in a first lead configuration. In an example, the first lead configuration can be selected by the controller 125. In other examples, the first lead configuration can be selected by a user and communicated to the controller 125 or to the implantable medical device 105.

In an example, at 1405, the first energy can be delivered using the first lead 210. The first electric field can be detected using the second lead 215. The second electric field can be detected using the first lead 210 and the second lead 215. In this example, the first lead configuration can include the first lead 210 and the second lead 215. In other examples, the first lead configuration can include other leads.

In certain examples, the first lead configuration can include the configuration illustrated in FIG. 2 or FIG. 3. In other examples, other lead configurations can be selected, including lead configurations including other leads, or lead configurations having different lead locations, such as at least one lead located in a different physical location (e.g., located in a different blood vessel), spatial location (such as located a certain distance from a prior location or another lead location), or other location.

At 1410, a second estimated defibrillation threshold can be calculated using at least one lead in a second lead configuration. Generally, the second lead configuration includes at least one lead not included in the first lead configuration, or the second lead configuration includes at least one lead located in a different location as the at least one lead of the first lead configuration (e.g., located in a different physical location, spatial location, or other location). In an example, the second lead configuration can be selected by the controller 125. In other examples, the second lead configuration can be selected by a user and communicated to the controller 125 or to the implantable medical device 105.

Generally, a first energy can be delivered, a first electric field can be detected, and a second electric field can be detected using the second lead configuration. In an example, at 1410, the second estimated defibrillation threshold can be calculated using the second lead configuration, such as calculating the second estimated defibrillation threshold using the delivered first energy, the detected first electric field, and the detected second electric field from the second lead configuration. In an example, the second estimated defibrillation threshold can be calculated using the controller 125.

At 1415, the second estimated defibrillation threshold can be compared to a specified value. In an example, the second estimated defibrillation threshold can be compared to the specified value in order to determine if the second estimated defibrillation threshold is above or below the specified value, or to determine if the estimated defibrillation threshold has changed. Generally, a change in the estimated defibrillation threshold can be indicative of a subject condition change, a system configuration change (e.g., electrode or lead tissue build-up, electrode or lead dislodgment, electrode or lead failure, other circuitry failure, etc.), or other change. In other examples, the second estimated defibrillation threshold can be compared to the specific value in order to ensure proper lead placement. Proper lead placement is generally lead placement that yields a reasonable estimated defibrillation threshold.

In certain examples, the specified value can include an average, typical, or other estimated or known defibrillation threshold. In other examples, the specified value can include a specified threshold, an absolute threshold, a device specific threshold, a safety-margin threshold, a baseline, or other specified value. In an example, the estimated defibrillation threshold can be compared to the specified value using the controller 125.

At 1420, a notification can be provided using information about at least one estimated defibrillation threshold or a detected electric field. In certain examples, the controller 125 or the notification module 426 can be configured to communicate information about at least one estimated defibrillation threshold, such as if the second estimated defibrillation threshold meets or exceeds the specified value, to a user. In other examples, the controller 125 or the notification module 426 can be configured to communicate information about a detected electric field (e.g., the detected second electric field).

In other examples, at least one lead configuration, such as the first lead configuration or the second lead configuration, can be selected using information from the controller 125 (e.g., the at least one estimated defibrillation threshold), from the first electric field detector 115 (e.g., the detected first electric field), the second electric field detector 120 (e.g., the detected second electric field), a remote server, a user interface, or other device.

In this document, an electric field, such as the first electric field or the second electric field, can include any electric field that can be detected in the subject, such as an intrinsic electric field established by normal cardiac or other electrical activity, an electric field established by an energy delivery circuit, e.g., the first energy delivery circuit 110, or other electric field.

In the examples of FIG. 1-14, various examples, including delivering a first energy, detecting a first electric field, detecting a second electric field, calculating an estimated defibrillation threshold, calculating an adjusted estimated defibrillation threshold, detecting a change in at lest one of the detected first electric field, the detected second electric field, and the estimated defibrillation threshold, providing a notification, selecting an electrode configuration, sensing a heart signal of a heart, sensing a respiration signal, and selecting a lead configuration are disclosed. It is to be understood that the disclosed examples are not exclusive, and can be implemented either alone or in combination, or in various permutations or combinations.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A system comprising:
an implantable energy delivery circuit configured to deliver a nondefibrillating and nonfibrillation-inducing energy to a first thoracic region;
a first implantable electric field detector configured to detect, in response to the nondefibrillating and nonfibrillation-inducing energy, a first electric field at a second thoracic region, wherein the second thoracic location includes a location in, on, or near at least one of a left apical region of the heart or a left ventricular free lateral wall of the heart;
a second implantable electric field detector configured to detect, in response to the same nondefibrillating and nonfibrillation-inducing energy, a second electric field between a third thoracic region and a fourth thoracic region, wherein the third thoracic region includes a location at or near at least a portion of the first thoracic region, and wherein the fourth thoracic location includes a location at or near at least a portion of the second thoracic region; and
an implantable or external controller configured to calculate an estimated defibrillation threshold using the nondefibrillating and nonfibrillation-inducing energy, the detected first electric field, and the detected second electric field.

2. The system of claim 1, wherein the implantable energy delivery circuit is configured to deliver the energy to the first thoracic region that includes a location in, on, or near at least one of a right ventricle of the heart, a superior vena cava, an internal pectoral region, or an internal abdominal region.

3. The system of claim 1, wherein the estimated defibrillation threshold is a function of the delivered energy, the detected first electric field, the detected second electric field, and a desired electric field strength.

4. The system of claim 3, wherein the estimated defibrillation threshold ("VDFT1$_{est}$") is calculated using $$VDFT1_{est} = V_1 \frac{A}{\nabla V_2} f(V_{3\text{-}4});$$

wherein $V_1$ includes a value of the delivered energy, A includes the desired electric field strength, $\nabla V_2$ includes the detected first electric field, and $V_{3\text{-}4}$ includes the detected second electric field; and
wherein $f(V_{3\text{-}4})$ is configured to adjust the ratio of $V_1$, A, and $\nabla V_2$.

5. The system of claim 1, wherein the controller is configured to calculate an initial estimated defibrillation threshold as a function of the delivered energy, the detected first electric field, and a desired electric field strength; and
wherein the estimated defibrillation threshold is a function of the initial estimated defibrillation threshold and the detected second electric field.

6. The system of claim 5, wherein the initial estimated defibrillation threshold ("VDFT$_{est}$") is calculated using $$VDFT_{est} = V_1 \frac{A}{\nabla V_2};$$

wherein $V_1$ includes a value of the delivered energy, A includes the desired electric field strength, and $\nabla V_2$ includes the detected first electric field; and
wherein the adjusted estimated defibrillation threshold ("VDFT$_{adj}$") is calculated using VDFT$_{adj}$=VDFT$_{est}$f$(V_{3\text{-}4})$, wherein $V_{3\text{-}4}$ the detected second electric field.

7. The system of claim 1, including:
at least one lead configured to couple at least one of the first energy delivery circuit, the first electric field detector, or the second electric field detector to at least one of the first thoracic region, the second thoracic region, the third thoracic region, or the fourth thoracic region; and
wherein the at least one lead includes at least one electrode.

8. The system of claim 7, wherein the at least one electrode is in a first electrode configuration; and wherein the controller is configured to calculate a second estimated defibrillation threshold using at least one electrode in a second electrode configuration, to compare the second estimated defibrillation threshold to another estimated defibrillation threshold, and to select an electrode configuration using at least one of the second estimated defibrillation threshold and the other estimated defibrillation threshold.

9. The system of claim 1, including a notification module configured to provide a notification using information from the controller.

10. The system of claim 1, comprising at least one of a heart signal sensing circuit and a respiration sensor, communicatively coupled to the controller, the heart signal sensing circuit configured to sense a heart signal of a heart, and the respiration sensor configured to sense a respiration signal, wherein the implantable energy delivery circuit is configured to deliver the energy at a specified portion of at least one of the heart signal of the heart and the respiration signal.

11. The system of claim 1, comprising at least one of a heart signal sensing circuit and a respiration sensor, communicatively coupled to the controller, the heart signal sensing circuit configured to sense a heart signal of a heart, and the respiration sensor configured to sense a respiration signal, wherein the first implantable electric field detector or the second implantable electric field detector is configured to detect an electric field at a specified portion of at least one of the heart signal of the heart and the respiration signal.

12. A method comprising:
delivering a nondefibrillating and nonfibrillation-inducing energy to a first thoracic region;
detecting a first electric field at a second thoracic region, in response to the nondefibrillating and nonfibrillation-inducing energy, wherein the second thoracic region includes a location in, on, or near at least one of a left apical region of the heart or a left ventricular free lateral wall of the heart;
detecting a second electric field between a third thoracic region and a fourth thoracic region, in response to the same nondefibrillating and nonfibrillation-inducing energy, wherein the third thoracic region includes a location at or near at least a portion of the first thoracic region, and wherein the fourth thoracic location includes a location at or near at least a portion of the second thoracic region; and
calculating an estimated defibrillation threshold using the delivered energy, the detected first electric field, and the detected second electric field.

13. The method of claim 12, wherein the delivering the first energy to a first thoracic region includes delivering the first energy in, on, or near at least one of a right ventricle of the heart, a superior vena cava, an internal pectoral region, or an internal abdominal region.

14. The method of claim 12, wherein the calculating the estimated defibrillation threshold includes calculating the estimated defibrillation threshold as a function of the delivered energy, the detected first electric field, the detected second electric field, and a desired electric field strength.

15. The method of claim 14, wherein the calculating the estimated defibrillation threshold ("VDFT1$_{est}$") includes using $$VDFT1_{est} = V_1 \frac{A}{\nabla V_2} f(V_{3\text{-}4});$$

wherein $V_1$ includes a value of the delivered energy, A includes the desired electric field strength, $\nabla V_2$ includes the detected first electric field, and $V_{3\text{-}4}$ includes the detected second electric field; and
wherein $f(V_{3\text{-}4})$ is configured to adjust the ratio of $V_1$, and A, $\nabla V_2$.

16. The method of claim 12, including calculating an initial estimated defibrillation threshold as a function of the delivered energy, the detected first electric field, and a desired electric field strength; and
wherein the calculating the estimated defibrillation threshold includes adjusting the initial estimated defibrillation threshold using the detected second electric field.

17. The method of claim 16, wherein the calculating the initial estimated defibrillation threshold ("VDFT$_{est}$") includes using $$VDFT_{est} = V_1 \frac{A}{\nabla V_2};$$

wherein $V_1$ includes a value of the delivered energy, A includes the desired electric field strength, and $\nabla V_2$ includes the detected first electric field; and
wherein the calculating the estimated defibrillation threshold ("VDFT$_{adj}$") is calculated using VDFT$_{adj}$=VDFT$_{est}$f($V_{3\text{-}4}$), wherein $V_{3\text{-}4}$ includes the detected second electric field.

18. The method of claim 12, wherein the delivering the energy, the detecting the first electric field, and the detecting the second electric field includes using at least one electrode in a first electrode configuration, the method including:
calculating a second estimated defibrillation threshold using at least one electrode in a second electrode configuration;
comparing the second estimated defibrillation threshold to another estimated defibrillation threshold; and
selecting an electrode configuration using at least one of the second estimated defibrillation threshold and the other estimated defibrillation threshold.

19. The method of claim 12, including providing a notification using information about at least one detected electric field.

20. The method of claim 12, comprising sensing at least one of a heart signal and a respiration signal;
wherein delivering the nondefibrillating and nonfibrillation-inducing energy to the first thoracic region includes delivering at a specified portion of at least one of the heart signal and the respiration signal; and
wherein detecting the first electric field or the second electric field includes detecting at a specified portion of at least one of the heart signal and the respiration signal.

* * * * *